US007235626B1

(12) United States Patent
Cochran et al.

(10) Patent No.: US 7,235,626 B1
(45) Date of Patent: Jun. 26, 2007

(54) STRUCTURED PEPTIDE SCAFFOLD FOR DISPLAYING TURN LIBRARIES ON PHAGE

(75) Inventors: Andrea G. Cochran, San Francisco, CA (US); Nicholas J. Skelton, San Mateo, CA (US); Melissa A. Starovasnik, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/592,695

(22) Filed: Jun. 13, 2000

Related U.S. Application Data

(60) Provisional application No. 60/139,017, filed on Jun. 14, 1999.

(51) Int. Cl.
*C07K 5/00* (2006.01)
*C07K 7/00* (2006.01)
(52) U.S. Cl. ............... 530/321; 530/317; 530/350; 530/300
(58) Field of Classification Search ............. 435/7.1, 435/6; 530/321, 317, 350, 7.1, 6, DIG. 24
See application file for complete search history.

(56) References Cited

U.S. PATENT DOCUMENTS

| 4,833,092 | A | 5/1989 | Geysen |
| 5,223,409 | A | 6/1993 | Ladner et al. |
| 5,534,615 | A | 7/1996 | Baker et al. |
| 5,627,024 | A | 5/1997 | Maruyama et al. |
| 5,766,905 | A | 6/1998 | Studier et al. |
| 5,821,047 | A | 10/1998 | Garrard et al. |
| 5,824,483 | A | 10/1998 | Houston, Jr. et al. |
| 5,830,851 | A | 11/1998 | Wrighton et al. |
| 5,866,341 | A | 2/1999 | Spinella et al. |
| 5,885,780 | A | 3/1999 | Olivera et al. |
| 6,013,458 | A | 1/2000 | Kahn et al. |
| 6,100,377 | A | 8/2000 | Greene |
| 6,180,343 | B1 | 1/2001 | Anderson et al. |
| 6,475,806 | B1 | 11/2002 | Benjamin et al. |
| 6,482,591 | B2 | 11/2002 | Lockhart et al. |

FOREIGN PATENT DOCUMENTS

| WO | WO 92/00091 | 1/1992 |
| WO | WO 94/03494 | 2/1994 |
| WO | WO 95/01800 | 1/1995 |
| WO | WO 95/34683 | 12/1995 |
| WO | WO 97/29185 | 8/1997 |
| WO | WO 98/49168 | 11/1998 |
| WO | WO 99/51625 | 10/1999 |
| WO | WO 00/20574 | 4/2000 |
| WO | WO 00/77194 | 12/2000 |
| WO | WO 01/91780 | 12/2001 |

OTHER PUBLICATIONS

Ball et al., "Conformational Constraints: Nonpeptide β-Turn Mimics" *Journal of Molecular Recognition* 3(2):55-64 (1990).
Bianchi et al., "High level expression and rational mutagenesis of a designed protein, the minibody. From an insoluble to a soluble molecule" *Journal of Molecular Biology* 236(2):649-659 (Feb. 18, 1994).
Christmann et al., "The cystine knot of a squash-type protease inhibitor as a structural scaffold for *Escherichia coli* cell surface display of conformationally constrained peptide" *Protein Engineering* 12(9):797-806 (Sep. 1999).
Cochran, A., "Antagonists of protein-protein interactions" *Chemistry and Biology* 7(4):R85-R94 (Apr. 2000).
Cwirla et al., "Peptide agonist of the thrombopoietin receptor as potent as the natural cytokine" *Science* 276(5319):1696-1699 (Jun. 13, 1997).
Fairbrother et al., "Novel Peptides Selected to Bind Vascular Endothelial Growth Factor Target the Receptor-Binding State" *Biochemistry* 37:17754-17764 (1998).
Falcomer et al., "Chain Reversals in Model Peptides: Studies of Cystine-Containing Cyclic Peptides. 3. Conformational Free Energies of Cyclization of Tetrapeptides of Sequence Ac-Cys-Pro-X-Cys-NHMe" *J. Am. Chem. Soc.* 114:4036-4042 (1992).
Favre et al., "Structural Mimicry of Canonical Conformations in Antibody Hypervariable Loops Using Cyclic Peptides Containing a Heterochiral Diproline Template" *J. Am. Chem. Soc.* 121:2679-2685 (1999).
Kieber-Emmons et al., "Therapeutic peptides and peptidomimetics" *Current Opinion in Biotechnology* 8(4):435-441 (Aug. 1997).
Ladner, R., "Constrained peptides as binding entities" *TIBTECH* 13:436-430 (Oct. 1995).
Lam et al., "A new type of synthetic peptide library for identifying ligand-binding activity" *Nature* 354:82-84 (1991).
Lin and Kim, "Urea Dependence of Thiol-Disulfide Equilibria in Thioredoxin: Confirmation of the Linkage Relationship and a Sensitive Assay for Structure" *Biochemistry* 28(12):5282-5287 (1989).
Livnah et al., "Functional mimicry of a protein hormone by a peptide agonist: the EPO receptor complex at 2.8 A" *Science* 273(5274):464-471 (Jul. 26, 1996).

(Continued)

*Primary Examiner*—T. D. Wessendorf
(74) *Attorney, Agent, or Firm*—Merchant & Gould P.C.

(57) ABSTRACT

The invention is directed to a model system for structure-activity analysis of peptide or protein molecules involved in important biological processes. Provided by the invention are combinatorial peptide libraries comprising disulfide-constrained cyclic peptides with sequences favorable for energy stabilized conformations. A preferred embodiment of the invention is directed to peptides containing β-turn tetrapeptide that form structured β-hairpin scaffold in solution. Methods of selecting and using such peptides are provided herein, which are useful for mimicking in vivo molecular interactions and designing therapeutic agents. Thus, the invention has profound utility for biological studies and drug development.

11 Claims, 11 Drawing Sheets

OTHER PUBLICATIONS

Lowman et al., "Molecular mimics of insulin-like growth factor 1 (IGF-1) for inhibiting IGF-1: IGF-binding protein interactions" *Biochemistry* 37(35):8870-8878 (Jun. 23, 1998).

Martin et al., "The affinity-selection of a minibody polypeptide inhibitor of human interleukin-6" *EMBO Journal* 13(22):5303-5309 (Nov. 15, 1994).

McBride et al., "Selection of Chymotrypsin Inhibitors from a Conformationally-constrained Combinatorial Peptide Library" *Journal of Molecular Biology* 259(4):819-827 (Jun. 21, 1996).

Milburn et al., "Chain Reversals in Model Peptides: Studies of Cystine-Containing Cyclic Peptides 1. Conformational Free Energies of Cyclization of Hexapeptides of Sequence Ac-Cys-X-Pro-Gly-Y-Cys-NHMe" *J. Am. Chem. Soc.* 109:4486-4496 (1987).

Milburn et al., "Chain reversals in model peptides: studies of cystine-containing cyclic peptides. II. Effects of valyl residues and possible i-to- (i+3) attractive ionic interactions on cyclization of [$Cys^1$], [$Cys^6$] hexapeptides" *International Journal of Peptide & Protein Research* 31(3):311-321 (Mar. 1988).

Milner-White, E., "Predicting the biologically active conformations of short polypeptides" *Trends in Pharmacological Sciences* 10(2):70-74 (Feb. 1989).

Myszka and Chaiken, "Design and characterization of an intramolecular antiparallel coiled coil peptide" *Biochemistry* 33(9):2363-2372 (Mar. 8, 1994).

Nygren and Uhlen, "Scaffolds for engineering novel binding sites in proteins" *Current Opinion in Structural Biology* 7(4):463-469 (Aug. 1997).

Smith and Pease, "Reverse turns in peptides and proteins" *CRC Critical Reviews in Biochemistry* 8(4):315-399 (1980).

Smith et al., "Small binding proteins selected from a combinatorial repertoire of knottins displayed on phage" *Journal of Molecular Biology* 277(2):317-332 (Mar. 27, 1998).

Stroup and Gierasch, "Reduced Tendency to Form a β Turn in Peptides from the P22 Tailspike Protein Correlates with a Temperature-Sensitive Folding Defect" *Biochemistry* 29:9765-9771 (1990).

Vita et al., "Novel miniproteins engineered by the transfer of active sites to small natural scaffolds" *Biopolymers* 47(1):93-100 (1998).

Vita et al., "Rational engineering of a miniprotein that reproduces the core of the CD4 site interacting with HIV-1 envelope glycoprotein" *Proc. Natl. Acad. Sci. USA* 96(23):13091-13096 (Nov. 9, 1999).

Wiesmann et al., "Crystal Structure of the Complex between VEGF and a Receptor-Blocking Peptide" *Biochemistry* 37:17765-17772 (1998).

Wrighton et al., "Small peptides as potent mimetics of the protein hormone erythropoietin" *Science* 273:458-463 (Jul. 26, 1996).

Barthe et al., "Synthesis and NMR solution structure of an α-helical hairpin stapled with two disulfide bridges" *Protein Science* (abstract only) 133:942-955 (2000).

Domingo et al., "Synthesis of a mixture of cyclic peptides based on the Bowman-Birk reactive site loop to screen for serine inhibitors" *International Journal or Protein and Peptide Research* 46:79-87 (1995).

Alexander et al., "Thermodynamic Analysis of the Folding of the *Streptococcal* Protein G igG-Binding Domains B1 and B2: Why Small Proteins Tend to have High Denaturation Temperatures", *Biochemistry*, 31:3597-3603 (1992).

Allen et al., "Finding prospective partners in the library: the two-hybrid system and phage display find a match", *TIBS*, 20:511-516 (1995).

Barbas, "Recent advances in phage display", *Current Opinion in Biochemistry*, 4:526-530 (1993).

Bass et al., "Hormone Phage: An Enrichment Method for Variant Proteins with Altered Binding Properties", *Proteins: Structure, Function, and Genetics*, 8(4):309-314 (1990).

Becktel and Schellman, "Protein Stability Curves", *Biopolymers*, 26:1859-1877 (1987).

Biachi et al., "A Conformationally Homogeneous Combinatorial Peptide Library", *J. Mol. Biol.*, 247:154-160 (1995).

Blanco et al., "A short linear peptide that folds into a native stable B-hairpin in aqueous solution", *Structural Biology*, 1(9):584-590 (Sep. 1994).

Bradbury and Cattaneo, "The use of phage display in neurobiology", *Trends in Neuroscience*, 18:243-249 (1995).

Choo and Klug, "Designing DNA-binding proteins on the surface of filamentous phage", *Current Opinion in Biotechnology*, 6:431-436 (1995).

Chothia, "Coiling of B-Pleated Sheets", *J. Mol. Biol.*, 163:107-117 (1983).

Clackson and Wells, "In vitro selection from protein and peptide librairies", *Trends Biotechnol.*, 12:173-184 (1994).

Clackson et al., "Making antibody fragments using phage display libraries", *Nature*, 352:624-628 (1991).

Cochran et al., "A Minimal Peptide Scaffold for B-Turn Display: Optimizing a Strand Position in Disulfide-Cyclized B-Hairpins", *J. Am. Chem. Soc.*, 123:625-632 (2001).

Cortese et al., "Identification of biologically active peptides using random libraries displayed on phage", *Current Opinion in Biotechnology*, 6:73-80 (1995).

Cortese et al., "Selection of biologically active peptides by phage display of random peptide libraries", *Current Opinion in Biotechnology*, 7:616-621 (1996).

Cunningham and Wells, "High-Resolution Epitope Mapping of hGH-Receptor Interactions by Alanine-Scanning Mutagenesis", *Science*, 244:1081-1085 (1989).

Cwirla et al., "Peptides on phage: a vast library of peptides for identifying ligands", *Proc. Natl. Acad. Sci. USA*, 87(16):6378-6832 (1990).

Dunn, I.S., "Phage display of proteins", *Current Opinion in Biotechnology*, 7:547-553 (1996).

Efimov et al., "Bacteriophage T4 as a Surface Display Vector", *Virus Genes*, 10(2):173-177 (1995).

Espinosa and Gellman, "A Designed B-Hairpin Containing a Natural Hydrophobic Cluster", *Agnew. Chem. Int. Ed.*, 39(13):2330-2333 (2000).

Felici, "Selection of antibody ligands from a large library of oligopeptides expressed on a multivalent exposition Vector", *J. Mol. Biol.*, 222:301-310 (1991).

Fowlkes et al., "Multipurpose Vectors for Peptide Expression on the M13 Viral Surface", *BioTechniques*, 13(3):422-427 (1992).

Gill and von Hippel, "Calculation of Protein Extinction Coefficients from Amino Acid Sequence Data", *Analytical Biochemistry*, 182:319-326 (1989).

Gram et al., "In vitro selection and affinity maturation of antibodies from a naive combinatorial immunoglobulin library", *Proc. Natl. Acad. Sci. USA*, 89(8):3576-3580 (1992).

Greenwood et al., "Peptides from Plasmodium Falciparum Circumsporozoite Protein as Antigens", *J. Mol. Bio.*, 220:821-827 (1991).

Gururaja et al., "A novel artificial loop scaffold for the noncovalent constraint for peptides", *Chem. & Biol.*, 7:515-527 (2000).

Havel, "An Evaluation of Computational Strategies for Use in the Determination of Protein Structure from Distance Constraints Obtained by Nuclear Magnetic Resonance", *Prog. Biophys. Molec. Biol.*, 56:43-78 (1991).

Hogrefe et al., "Cloning in a bacteriophage lambda vector for the display of binding proteins in filamentous phage", *Gene*, 137:85-91 (1993).

Honda et al., "Thermodynamics of a B-Hairpin Structure: Evidence for Cooperative Formation of Folding Nucleus", *J. Mol. Biol.*, 295:269-278 (2000).

Hoogenboom et al., "Multi-subunit proteins on the surface of filamentous phage: methodologies for displaying antibody (Fab) heavy and light chains", *Nucleic Acids Research*, 19(15):4133-4137 (1991).

Iannolo et al., "Modifying Filamentous Phage Capsid: Limits in the Size of the Major Capsid Protein", *J. Mol. Biol.*, 248:835-844 (1995).

Jiang et al., "Display of a PorA peptide from Neisseria meningitidis on the bacteriophage T4 capsid surface", *Chemical Abstracts*, (Abstract No. 44380q) 128(5):147 (1998).

Johnson et al., "Analysis of Data from the Analytical Ultracentrifuge by Nonlinear Least-Squares Techniques", *Biophys. J.*, 36:575-588 (Dec. 1981).

Kang et al., "Linkage of recognition and replication functions by assembling combinatorial antibody Fab libraries along phage surfaces", *Proc. Natl. Acad. Sci. USA*, 88:4363-4366 (1991).

Karle et al., "Cyclic Cystine Peptides. Antiparallel B-Sheet Conformation for the 2-Membered Ring in Boc-Cys-Val-Aib-Ala-Leu-Cys-NHMe", *American Chemical Society*, 110:1958-1963 (1988).

Kessler et al., "Peptide Conformation. 42.[1,2] Conformation of Side Chains in Peptides Using Heteronuclear Coupling Constants Obtained by Two-Dimensional NMR Spectroscopy", *J. Am. Chem. Soc.*, 109:6927-6933 (1987).

Kortemme et al., "Design of a 20-Amino Acid, Three-Stranded B-Sheet Protein", *Science*, 281:253-256 (Jul. 10, 1998).

Lindqvist and Naderi, "Peptide presentation by bacteriophage P4", *FEMS Microbiology Reviews*, 17:33-39 (1995).

Lowman and Wells. "Monovalent Phage Display: A method for Selecting Variant Proteins from Random Libraries", *Methods: Comp. to Methods Enzymol.*, 3(3):205-216 (1991).

Lowman et al., "Selecting High-Affinity Binding Proteins by Monovalent Phage Display", *Biochemistry*, 30(45):10832-10838 (1991).

Makowski, L., "Structural constraints on the display of foreign peptides on filamentous bacteriophages", *Gene*, 128:5-11 (1993).

Malik and Perham, "New vectors for peptide display on the surface of filamentous bacteriophage", *Gene*, 171:49-51 (1996).

Markland et al., "Design, construction and function of a multicopy display vector using fusions to the major coat protein of bacteriophage M13", *Gene*, 109:13-19 (1991).

Marks et al., "By-passing immunization: human antibodies from V-gene libraries displayed on phage", *J. Mol. Biol.*, 222:581-597 (1991).

McCafferty et al., "Phage antibodies: filamentous phage displaying antibody variable domains", *Nature*, 348:552-554 (1990).

McGregor, "Selection of proteins and peptides from libraries displayed on filamentous bacteriophage", *Molecular Biotechnology*, 6:155-162 (1995).

McLafferty et al., "M13 bacteriophage displaying disulfide-constrained microproteins", *Gene*, 128:29-36 (1993).

Merrifield, R.B., "Solid Phase Peptide Synthesis. I. The Synthesis of a Tetrapeptide", *J. Am. Chem. Soc.*, 85:2149-2154 (1963).

Minor and Kim, "Measurement of the B-sheet-forming propensities of amino acids", *Nature*, 367:660-663 (Feb. 17, 1994).

Munoz et al., "Folding dynamics and mechanism of B-hairpin formation", *Nature*, 390:196-199 (Nov. 13, 1997).

O'Boyle et al., "Identification of a novel peptide substrate of HSV-1 protease using substrate phage display", *Virology*, 236:338-347 (1997).

O'Neil and Hoess, "Phase display: protein engineering by directed evolution", *Current Opinion in Structural Biology*, 5:443-449 (1995).

Privalov and Gill, "Stability of Protein Structure and Hydrophobic Interaction", *Advances in Protein Chemistry*, 39:191-234 (1988).

Ramirez-Alvarado et al., "B-Hairpin and B-Sheet Formation in Designed Linear Peptides", *Bioorganic & Medicinal Chemistry*, 7:93-103 (1999).

Ramirez-Alvarado et al., "Conformational analysis of peptides corresponding to all the secondary structure elements of protein L B1 domain: Secondary structure propensities are not conserved in proteins with the same fold", *Protein Science*, 6:162-174 (1997).

Ramirez-Alvarado et al., "De novo design and structural analysis of a model B-hairpin peptide system", *Nature Structural Biology*, 3(7):604-612 (Jul. 1996).

Ramirez-Alvarado et al., "Role of B-Turn Residues in B-Hairpin Formation and Stability in Designed Peptides", *J. Mol. Biol.*, 273:898-912 (1997).

Ren et al., "Cloining of linear DNAs in vivo by overexpressed T4 DNA ligase: construction of a T4 phage hoc gene display vector", *Chemical Abstracts*, (Abstract No. 215644q) 127(16):155 (1997).

Ren et al., "Phage display of intact domains at high copy number: A system based on SOC, the small outer capsid protein of bacteriophage T4", *Protein Science*, 5:1833-1843 (1996).

Ren et al., "Phage T4 SOC and HOC display of biologically active, full-length proteins on the viral capsid", *Gene*, 215-439-444 (1998).

Rietman et al., "The solution structure of the synthetic circular peptide CGVSRQGKPYC NMR studies of the folding of a synthetic model for the DNA-binding loop of the ssDNA-binding protein encoded by gene V of phage M13", *Eur. J. of Biochem.*, 238:706-713 (1996).

Russell and Cochran, "Designing Stable B-Hairpins: Energetic Contributions from Cross-Strand Residues", *J. Am. Chem. Soc.*, 122:12660-12601 (2000).

Scott and Smith, "Searching for peptide ligands with an epitope library", *Science*, 249:386-390 (1990).

Sibanda et al., "Conformation of B-Hairpins in Protein Structures", *J. Mol. Biol.*, 206:759-777 (1989).

Skelton et al., "Determination of the Solution Structure of the Peptide Hormone Guanylin: Observation of a Novel Form of Topological Stereoisomerism", *Biochemistry*, 33:13581-13592 (1994).

Smith and Scott, "Libraries of Peptides and Proteins Displayed on Filamentous Phage", *Methods in Enzymology*, 217:228-257 (1993).

Smith, "Surface display and peptide libraries", *Gene*, 128:1-2 (1993).

Smith, G.P., "Surface presentation of protein epitopes using bacteriophage expression systems", *Curr. Opin. Biotechnol.*, 2(5):668-673 (1991).

Soumillion et al., "Phage display of enzymes and in vitro selection for catalytic activity", *Applied Biochemistry and Biotechnology*, 47:175-190 (1994).

Stanger and Gellman, "Rules for Antiparallel B-Sheet Design: D-Pro-Gly is Superior to L-Asn-Gly for B-Hairpin Nucleation", *J. Am. Chem. Soc.*, 120:4236-4237 (1998).

Syud et al., "NMR-Based Quantification of B-Sheet Populations in Aqueous Solution through Use of Reference Peptides for the Folded and Unfold States", *J. Am. Chem. Soc.*, 121:11577-11578 (1999).

Thennarasu and Nagaraj, "Synthetic Peptides Corresponding to the B-Hairpin Loop of Rabbit Defensin NP-2 Show Antimicrobial Activity", *Biochem. & Biophys. Res. Comm.*, 254:281-283 (1999).

Walse et al., "Structure of a cyclic peptide with a catalytic triad, determined by computer simulation and NMR spectroscopy", *J. Comput. Aided Mol. Des.*, 10:11-22 (1996).

Wells et al., "Cassette Mutagenesis: an Efficient Method for Generation of Multiple Mutations at Defined Sites", *Gene*, 34(2-3):315-323 (1985).

Zerella et al., "Autonomous folding of a peptide corresponding to the N-terminal B-hairpin from ubiquitin", *Protein Science*, 8:1320-1331 (1999).

Zerella et al., "Structural characterization of a mutant peptide derived from ubiquitin: Implications for protein folding", *Protein Science*, 9:2142-2150 (2000).

Zhang et al., "Synthetic CD4 exocyclic peptides antagonize CD4 holoreceptor binding and T cell activation", *Nature Biotechnology*, 14:472-475 (Apr. 1996).

Zhang et al., "Synthetic CD4 exocyclics inhibit binding of human immunodeficiency virus type 1 envelope to CD4 and virus replication in T lymphocytes", *Nature Biotechnology*, 15(2):150-154 (Feb. 1997).

Zhong, "Conformational Mimicry of a Chlamydial Neutralization Epitope on Filamentous Phage", *Journal of Biological Chemistry*, 269(39):24183-24188 (1994).

Zoller and Smith, "Oligonucleotide-directed Mutagenesis Using M13-derived Vectors: An Efficient and General Procedure for the Production of Point Mutations in Any Fragment of DNA", *Nucl. Acids Res.*, 10(20):6487-6500 (1982).

Blanco, F. et al., "NMR Evidence of a Short Linear Peptide That Folds into a β-Hairpin in Aqueous Solution," *J. Am. Chem. Soc.*, 115(13):5887-5888 (1993).

Chou, P. et al., "Empirical Predictions Of Protein Conformation," *Am. Rev. Biochem.*, 47:251-276 (1978).

Constantine, K. et al., "Structural and Dynamic Properties of a β-Hairpin-Forming Linear Peptide. 1. Modeling Using Ensemble-Averaged Constraints," *J. Am. Chem. Soc.*, 117(44):10841-10854 (1995).

de Alba, E. et al., "Conformational investigation of designed short linear peptides able to fold into β-hairpin structures in aqueous solution," *Folding & Design*, 1(2):133-144 (Feb. 26, 1996).

de Alba, E. et al., "Cross-strand side-chain interactions versus turn conformation in β-hairpins," *Protein Science*, 6:2548-2560 (1997).

de Alba, E. et al., "Interactions responsible for the pH dependence of the β-hairpin conformational population formed by a designed linear peptide," *Eur. J. Biochem.*, 233:283-292 (1995).

de Alba, E. et al., "Turn Residue Sequence Determines β-Hairpin Conformation in Designed Peptides," *J. Am. Chem. Soc.*, 119(1):175-183 (1997).

Friedrichs, M. et al., "Structural and Dynamic Properties of a β-Hairpin-Forming Linear Peptide. 2. $^{13}$C NMR Relaxation Analysis," *J. Am. Chem. Soc.*, 117(44):10855-10864 (1995).

Griffiths-Jones, S. et al., "Dissecting the Stability of a β-Hairpin Peptide that Folds in Water: NMR and Molecular Dynamics Analysis of the β-Turn and β-Strand Contributions to Folding," *J. Mol. Biol.*, vol. 292, pp. 1051-1069 (1999).

Griffiths-Jones, S. et al., "NMR evidence for the nucleation of a β-hairpin peptide conformation in water by an Asn-Gly type I' β-turn sequence," *Chem. Commun.*, pp. 789-790 (1998).

Haque, T. et al., "Insights on β-Hairpin Stability in Aqueous Solution from Peptides with Enforced type I' and Type II' β-Turns," *J. Am. Chem. Soc.*, 119:2303-2304 (1997).

Hutchinson, E. et al., "Determinants of strand register in antiparallel β-sheets of proteins," *Protein Science*, 7:2287-2300 (1998).

Kim, C. et al., "Thermodynamic β-sheet propensities measured using a zinc-finger host peptide," *Nature*, 362:267-270 (Mar. 18, 1993).

Kobayashi, N. et al., "Fragment Reconstitution of a Small Protein: Disulfide Mutant of a Short C-Terminal Fragment Derived from *Streptococcal* Protein G," *Biochemistry*, 38(11):3228-3234 (1999).

Kobayashi, N. et al., "Role of Side-chains in the Cooperative β-Hairpin Folding of the Short C-Terminal Fragment Derived from *Streptococcal* Protein G," *Biochemistry*, 39(21): 6564-6571 (2000).

Mattos, C. et al., "Analysis of Two-residue Turns in Proteins," *J. Mol. Biol.*, 238:733-747 (1994).

Maynard, A. et al., "NMR structural analysis of a β-hairpin peptide designed for DNA binding," *Chem. Commun.*, pp. 1297-1298 (1997).

Maynard, A. et al., "Origin of β-Hairpin Stability in Solution: Structural and Thermodynamic Analysis of the Folding of a Model Peptide Supports Hydrophobic Stabilization in Water," *J. Am. Chem. Soc.*, 120(9):1996-2007 (1998).

Minor, Jr., D. et al., "Context is a major determinant of β-sheet propensity," *Nature*, 371:264-267 (Sep. 15, 1994).

Minor, Jr., D. et al., "Measurement of the β-sheet-forming propensities of amino acids," *Nature*, 367:660-663 (Feb. 17, 1994).

Muñoz, V. et al., "Intrinsic Secondary Structure Propensities of the Amino Acids, Using Statistical Φ-Ψ Matrices: Comparison With Experimental Scales," *Proteins: Structure, Function, and Genetics*, 20:301-311 (1994).

Ried, C. et al., "High Affinity Endotoxin-binding and Neutralizing Peptides Based on the Crystal Structure of Recombinant *Limulus* Anti-lipopolysaccharide Factor," *Journal of Biological Chemistry*, 271(45):28120-28127 (Nov. 8, 1996).

Rohrer, S. et al., "Rapid Identification of Subtype-Selective Agonists of the Somatostatin Receptor Through Combinatorial Chemistry," *Science*, 282:737-740 (Oct. 23, 1998).

Searle, M. et al., "A short linear peptide derived from the N-terminal sequence of ubiquitin folds into a water-stable non-native β-hairpin," *Nature Structural Biology*, 2(11):999-1006 (Nov. 1995).

Smith, C. et al., "A Thermodynamic Scale for the β-Sheet Forming Tendencies of the Amino Acids," *Biochemistry*, 33(18):5510-5517 (1994).

Smith, C. et al., "Guidelines for Protein Design: The Energetics of β Sheet Side Chain Interactions," *Science*, 270:980-982 (Nov. 10, 1995).

Syud, F. et al., "Interstrand Side Chain-Side Chain Interactions in a Designed β-Hairpin: Significance of Both Lateral and Diagonal Pairings," *J. Am. Chem. Soc.*, 123(36):8667-8677 (2001).

Wouters, M. et al., "An Analysis of Side Chain Interactions and Pair Correlations Within Antiparallel β-Sheets: The Differences Between Backbone Hydrogen-Bonded and Non-Hydrogen-Bonded Residue Pairs," *Proteins: Structure, Function, and Genetics*, 22:119-131 (1995).

Kayagaki, N. et al., "BAFF/BLyS Receptor 3 Binds the B Cell Survival Factor BAFF Ligand through a Discrete Surface Loop and Promotes Processing of NF-kB2," *Immunity*, vol. 10, pp. 515-524 (Oct. 2002).

A

B

A

B

SEQUENCE LISTING

```
<160> NUMBER OF SEQ ID NOS: 49

<210> SEQ ID NO 1
<211> LENGTH: 18
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 2, 16
<223> OTHER INFORMATION: Xaa is Trp, Tyr, Phe, His, Ile, Val or Thr.
<220> FEATURE:
<221> NAME/KEY: UNSURE
<222> LOCATION: 3, 17
<223> OTHER INFORMATION: Xaa is Trp, Tyr, Phe, Leu, Met, Ile or Val.
<220> FEATURE:
<221> NAME/KEY: UNSURE
<222> LOCATION: 4-15
<223> OTHER INFORMATION: Xaa is a naturally occurring L-amino acid and 9
      may be absent.

<400> SEQUENCE: 1

Cys Xaa Xaa Xaa Xaa Xaa Xaa Xaa Xaa Xaa Xaa Xaa Xaa Xaa Xaa Xaa Xaa Cys
 1               5                  10                  15

<210> SEQ ID NO 2
<211> LENGTH: 10
<212> TYPE: PRT
<213> ORGANISM: Artificial Sequence
<220> FEATURE:
<223> OTHER INFORMATION: turn peptide

<400> SEQUENCE: 2

Cys Thr Trp Glu Gly Asn Lys Leu Thr Cys
 1               5                  10

<210> SEQ ID NO 3
<211> LENGTH: 12
<212> TYPE: PRT
```

```
<213> ORGANISM: Artificial Sequence
<220> FEATURE:
<223> OTHER INFORMATION: turn peptide

<400> SEQUENCE: 3

Ser Cys Thr Trp Glu Gly Asn Lys Leu Thr Cys Lys
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: turn peptide

<400> SEQUENCE: 4

Cys Gly Asn Gln Gly Ser Phe Leu Thr Cys
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: turn peptide

<400> SEQUENCE: 5

Cys Thr Trp Gln Gly Ser Phe Leu Thr Cys
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: turn peptide

<400> SEQUENCE: 6

Ser Cys Gly Asn Gln Gly Ser Phe Leu Thr Cys Lys
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: turn peptide

<400> SEQUENCE: 7

Ser Cys Thr Asn Gln Gly Ser Phe Leu Thr Cys Lys
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: turn peptide

<400> SEQUENCE: 8

Ser Cys Gly Trp Gln Gly Ser Phe Leu Thr Cys Lys
 1               5                  10

<210> SEQ ID NO 9
<211> LENGTH: 12
<212> TYPE: PRT
<213> ORGANISM: Artificial Sequence
```

```
<220> FEATURE:
<223> OTHER INFORMATION: turn peptide

<400> SEQUENCE: 9

Ser Cys Thr Trp Gln Gly Ser Phe Leu Thr Cys Lys
  1               5                  10

<210> SEQ ID NO 10
<211> LENGTH: 12
<212> TYPE: PRT
<213> ORGANISM: Artificial Sequence
<220> FEATURE:
<223> OTHER INFORMATION: turn peptide

<400> SEQUENCE: 10

Met Cys Gly Asn Gln Gly Met Phe Leu Thr Cys Lys
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: turn peptide

<400> SEQUENCE: 11

Met Cys Thr Trp Gln Gly Met Phe Leu Thr Cys Lys
  1               5                  10

<210> SEQ ID NO 12
<211> LENGTH: 10
<212> TYPE: PRT
<213> ORGANISM: Artificial Sequence
<220> FEATURE:
<223> OTHER INFORMATION: turn peptide

<400> SEQUENCE: 12

Cys Thr Lys Val Trp Gln Leu Trp Thr Cys
  1               5                  10

<210> SEQ ID NO 13
<211> LENGTH: 12
<212> TYPE: PRT
<213> ORGANISM: Artificial Sequence
<220> FEATURE:
<223> OTHER INFORMATION: turn peptide

<400> SEQUENCE: 13

Ser Cys Thr Trp Val Trp Gln Leu Leu Thr Cys Lys
  1               5                  10

<210> SEQ ID NO 14
<211> LENGTH: 12
<212> TYPE: PRT
<213> ORGANISM: Artificial Sequence
<220> FEATURE:
<223> OTHER INFORMATION: turn peptide

<400> SEQUENCE: 14

Ser Cys His Phe Gly Pro Leu Thr Trp Val Cys Lys
  1               5                  10

<210> SEQ ID NO 15
<211> LENGTH: 12
<212> TYPE: PRT
<213> ORGANISM: Artificial Sequence
<220> FEATURE:
```

<223> OTHER INFORMATION: turn peptide

<400> SEQUENCE: 15

Ser Cys Thr Trp Gly Pro Leu Thr Leu Thr Cys Lys
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 3
<223> OTHER INFORMATION: Xaa is Trp, Tyr, Leu, Val, Thr or Asp.

<400> SEQUENCE: 16

Cys Thr Xaa Glu Gly Asn Lys Leu Thr Cys
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 3
<223> OTHER INFORMATION: Xaa is Trp, Tyr, Leu, Val, Thr or Asp.

<400> SEQUENCE: 17

Cys Thr Xaa Glu Asn Gly Lys Leu Thr Cys
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 3
<223> OTHER INFORMATION: Xaa is Trp, Tyr, Leu, Val, Thr or Asp.
<220> FEATURE:
<221> NAME/KEY: UNSURE
<222> LOCATION: 5
<223> OTHER INFORMATION: Pro is D-Pro.

<400> SEQUENCE: 18

Cys Thr Xaa Glu Pro Asn Lys Leu Thr Cys
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 3
<223> OTHER INFORMATION: Xaa is Trp, Tyr, Leu, Val, Thr or Asp.
<220> FEATURE:
<221> NAME/KEY: UNSURE
<222> LOCATION: 5
<223> OTHER INFORMATION: Pro is D-Pro.

<400> SEQUENCE: 19

```
Cys Thr Xaa Glu Pro Gly Lys Leu Thr Cys
 1               5                  10
```

<210> SEQ ID NO 20
<211> LENGTH: 10
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 3
<223> OTHER INFORMATION: Xaa is Trp, Tyr, Phe, Leu, Met, Ile, Val or
      Ala.

<400> SEQUENCE: 20

```
Cys Thr Xaa Glu Gly Asn Lys Leu Thr Cys
 1               5                  10
```

<210> SEQ ID NO 21
<211> LENGTH: 10
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 8
<223> OTHER INFORMATION: Xaa is Trp, Tyr, Phe, Leu, Met, Ile, Val or
      Ala.

<400> SEQUENCE: 21

```
Cys Thr Leu Glu Gly Asn Lys Xaa Thr Cys
 1               5                  10
```

<210> SEQ ID NO 22
<211> LENGTH: 10
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 3
<223> OTHER INFORMATION: Xaa is Trp, Tyr, Phe, Leu, Met, Ile, Val or
      Ala.

<400> SEQUENCE: 22

```
Cys Thr Xaa Glu Gly Asn Lys Trp Thr Cys
 1               5                  10
```

<210> SEQ ID NO 23
<211> LENGTH: 10
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 8
<223> OTHER INFORMATION: Xaa is Trp, Tyr, Phe, Leu, Met, Ile, Val or
      Ala.

<400> SEQUENCE: 23

```
Cys Thr Trp Glu Gly Asn Lys Xaa Thr Cys
 1               5                  10
```

<210> SEQ ID NO 24
<211> LENGTH: 102

```
<212> TYPE: DNA
<213> ORGANISM: Artificial Sequence
<220> FEATURE:
<223> OTHER INFORMATION: synthesized sequence

<400> SEQUENCE: 24
taataataaa tggctgatcc gaaccgtttc cgcggtaaag atctgggtgg         50
cggtactcca acgacccgc caaccactcc accaactgat agcccaggcg         100
gt                                                            102

<210> SEQ ID NO 25
<211> LENGTH: 72
<212> TYPE: DNA
<213> ORGANISM: Artificial Sequence
<220> FEATURE:
<223> OTHER INFORMATION: Synthesized sequence.
<220> FEATURE:
<221> NAME/KEY: unsure
<222> LOCATION: 19-20, 31-32, 34-35, 37-38, 40-41, 52-53
<223> OTHER INFORMATION: unknown base

<400> SEQUENCE: 25
tccgcctcgg cttatgcann stgcacttgg nnsnnsnnsn nsctgacttg         50
tnnsatggct gatccgaacc gt                                      72

<210> SEQ ID NO 26
<211> LENGTH: 9
<212> TYPE: PRT
<213> ORGANISM: Artificial Sequence
<220> FEATURE:
<223> OTHER INFORMATION: turn peptide

<400> SEQUENCE: 26

Tyr Gln Asn Pro Asp Gly Ser Gln Ala
 1               5

<210> SEQ ID NO 27
<211> LENGTH: 10
<212> TYPE: PRT
<213> ORGANISM: Artificial Sequence
<220> FEATURE:
<223> OTHER INFORMATION: turn peptide

<400> SEQUENCE: 27

Ile Tyr Ser Asn Pro Asp Gly Thr Trp Thr
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: turn peptide

<400> SEQUENCE: 28

Ile Tyr Ser Asn Ser Asp Gly Thr Trp Thr
 1               5                  10

<210> SEQ ID NO 29
<211> LENGTH: 10
<212> TYPE: PRT
<213> ORGANISM: Artificial Sequence
<220> FEATURE:
<223> OTHER INFORMATION: turn peptide

<400> SEQUENCE: 29
```

```
Ile Thr Ser Asn Ser Asp Gly Thr Trp Thr
1               5                   10
```

<210> SEQ ID NO 30
<211> LENGTH: 10
<212> TYPE: PRT
<213> ORGANISM: Artificial Sequence
<220> FEATURE:
<223> OTHER INFORMATION: turn peptide

<400> SEQUENCE: 30

```
Tyr Ile Thr Asn Ser Asp Gly Thr Trp Thr
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: turn peptide

<400> SEQUENCE: 31

```
Arg Gly Ile Thr Val Asn Gly Lys Thr Tyr Gly Arg
1               5                   10
```

<210> SEQ ID NO 32
<211> LENGTH: 12
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 6
<223> OTHER INFORMATION: Xaa is D-Pro or L-Asn.
<220> FEATURE:
<221> NAME/KEY: UNSURE
<222> LOCATION: 8
<223> OTHER INFORMATION: Xaa is Orn.

<400> SEQUENCE: 32

```
Arg Tyr Val Glu Val Xaa Gly Xaa Lys Ile Leu Gln
1               5                   10
```

<210> SEQ ID NO 33
<211> LENGTH: 16
<212> TYPE: PRT
<213> ORGANISM: Artificial Sequence
<220> FEATURE:
<223> OTHER INFORMATION: turn peptide

<400> SEQUENCE: 33

```
Lys Lys Tyr Thr Val Ser Ile Asn Gly Lys Lys Ile Thr Val Ser
1               5                   10                  15

Ile
```

<210> SEQ ID NO 34
<211> LENGTH: 16
<212> TYPE: PRT
<213> ORGANISM: Artificial Sequence
<220> FEATURE:
<223> OTHER INFORMATION: turn peptide

<400> SEQUENCE: 34

```
Gly Glu Trp Thr Tyr Asp Asp Ala Thr Lys Thr Phe Thr Val Thr
1               5                   10                  15
```

Glu

```
<210> SEQ ID NO 35
<211> LENGTH: 8
<212> TYPE: PRT
<213> ORGANISM: Artificial Sequence
<220> FEATURE:
<223> OTHER INFORMATION: turn peptide

<400> SEQUENCE: 35

Ala Cys Ser Pro Gly His Cys Glu
 1               5

<210> SEQ ID NO 36
<211> LENGTH: 11
<212> TYPE: PRT
<213> ORGANISM: Artificial Sequence
<220> FEATURE:
<223> OTHER INFORMATION: turn peptide

<400> SEQUENCE: 36

Cys Gly Val Ser Arg Gln Gly Lys Pro Tyr Cys
 1               5                  10

<210> SEQ ID NO 37
<211> LENGTH: 16
<212> TYPE: PRT
<213> ORGANISM: Artificial Sequence
<220> FEATURE:
<223> OTHER INFORMATION: turn peptide

<400> SEQUENCE: 37

Gly Cys Lys Pro Thr Phe Arg Arg Leu Lys Trp Lys Tyr Lys Cys
 1               5                  10                  15

Gly

<210> SEQ ID NO 38
<211> LENGTH: 18
<212> TYPE: PRT
<213> ORGANISM: Artificial Sequence
<220> FEATURE:
<223> OTHER INFORMATION: turn peptide

<400> SEQUENCE: 38

Cys Ala Gly Phe Met Arg Ile Arg Gly Arg Ile His Pro Leu Cys
 1               5                  10                  15

Met Arg Arg

<210> SEQ ID NO 39
<211> LENGTH: 10
<212> TYPE: PRT
<213> ORGANISM: Artificial Sequence
<220> FEATURE:
<223> OTHER INFORMATION: turn peptide

<400> SEQUENCE: 39

Phe Cys Asn Gln Gly Ser Phe Leu Cys Tyr
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: turn peptide
```

```
<400> SEQUENCE: 40

Phe Cys Tyr Ile Cys Glu Val Glu Asp Gln Cys Tyr
 1               5                  10

<210> SEQ ID NO 41
<211> LENGTH: 16
<212> TYPE: PRT
<213> ORGANISM: Artificial Sequence
<220> FEATURE:
<223> OTHER INFORMATION: turn peptide

<400> SEQUENCE: 41

Met Gln Ile Gly Val Lys Asn Pro Asp Gly Thr Ile Thr Leu Glu Val
 1               5                  10                  15

<210> SEQ ID NO 42
<211> LENGTH: 15
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 7
<223> OTHER INFORMATION: Xaa is Pro.
<220> FEATURE:
<221> NAME/KEY: UNSURE
<222> LOCATION: 8
<223> OTHER INFORMATION: Xaa is Ala or Gly.

<400> SEQUENCE: 42

Met Gln Ile Gly Val Lys Xaa Xaa Lys Thr Ile Thr Leu Glu Val
 1               5                  10                  15

<210> SEQ ID NO 43
<211> LENGTH: 6
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 2, 5
<223> OTHER INFORMATION: Xaa is any amino acid.

<400> SEQUENCE: 43

Cys Xaa Pro Gly Xaa Cys
 1               5

<210> SEQ ID NO 44
<211> LENGTH: 4
<212> TYPE: PRT
<213> ORGANISM: Artificial Sequence
<220> FEATURE:
<223> OTHER INFORMATION: turn peptide

<400> SEQUENCE: 44

Glu Gly Asn Lys
 1

<210> SEQ ID NO 45
<211> LENGTH: 4
<212> TYPE: PRT
<213> ORGANISM: Artificial Sequence
<220> FEATURE:
<223> OTHER INFORMATION: turn peptide

<400> SEQUENCE: 45

Glu Asn Gly Lys
```

<210> SEQ ID NO 46
<211> LENGTH: 4
<212> TYPE: PRT
<213> ORGANISM: Artificial Sequence
<220> FEATURE:
<223> OTHER INFORMATION: turn peptide

<400> SEQUENCE: 46

Gln Gly Ser Phe

<210> SEQ ID NO 47
<211> LENGTH: 4
<212> TYPE: PRT
<213> ORGANISM: Artificial Sequence
<220> FEATURE:
<223> OTHER INFORMATION: turn peptide

<400> SEQUENCE: 47

Val Trp Gln Leu

<210> SEQ ID NO 48
<211> LENGTH: 4
<212> TYPE: PRT
<213> ORGANISM: Artificial Sequence
<220> FEATURE:
<223> OTHER INFORMATION: turn peptide

<400> SEQUENCE: 48

Gly Pro Leu Thr

<210> SEQ ID NO 49
<211> LENGTH: 118
<212> TYPE: PRT
<213> ORGANISM: Artificial Sequence
<220> FEATURE:
<223> OTHER INFORMATION: turn peptide
<220> FEATURE:
<221> NAME/KEY: UNSURE
<222> LOCATION: 1-50
<223> OTHER INFORMATION: Xaa is any naturally occurring amino acid, and
      all but one may be missing.
<220> FEATURE:
<221> NAME/KEY: UNSURE
<222> LOCATION: 52
<223> OTHER INFORMATION: Xaa is Trp, Tyr, Phe, His, Ile, Val, or Thr.
<220> FEATURE:
<221> NAME/KEY: UNSURE
<222> LOCATION: 54-65
<223> OTHER INFORMATION: Xaa is a naturally occurring L-amino acid and
      all but 3 may be missing.
<220> FEATURE:
<221> NAME/KEY: UNSURE
<222> LOCATION: 67
<223> OTHER INFORMATION: Xaa is Trp, Tyr, Phe, His, Ile, Val, or Thr.
<220> FEATURE:
<221> NAME/KEY: UNSURE
<222> LOCATION: 69-118
<223> OTHER INFORMATION: Xaa is a naturally occurring amino acid and all
      but one may be missing.

<400> SEQUENCE: 49

Xaa Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa Xaa Xaa
        20                  25                  30                  35

Xaa Xaa Xaa Xaa Xaa Xaa Xaa Xaa Xaa Xaa Xaa Xaa Xaa Xaa Cys Xaa Trp Xaa
            40                  45                  50

```
Xaa Xaa Xaa Xaa Xaa Xaa Xaa Xaa Xaa Xaa Xaa Trp Xaa Cys Xaa Xaa Xaa Xaa
 55              60              65              70

Xaa Xaa Xaa Xaa Xaa Xaa Xaa Xaa Xaa Xaa Xaa Xaa Xaa Xaa Xaa Xaa
        75              80              85              90

Xaa Xaa Xaa Xaa Xaa Xaa Xaa Xaa Xaa Xaa Xaa Xaa Xaa Xaa Xaa Xaa
            95             100             105

Xaa Xaa Xaa Xaa Xaa Xaa Xaa Xaa Xaa Xaa
   110                115
```

STRUCTURED PEPTIDE SCAFFOLD FOR DISPLAYING TURN LIBRARIES ON PHAGE

This application claims priority under 35 U.S.C. 119(e) to the U.S. provisional application Ser. No. 60/139,017, filed Jun. 14, 1999, the disclosure of which is expressly incorporated herein by reference in its entirety.

TECHNICAL FIELD

The present invention relates in general to protein structure-activity relationship studies, and in particular to combinatorial libraries of conformationally-constrained peptides and methods of generating and screening such libraries for biological and pharmaceutical use.

BACKGROUND ART

Structure-Activity Relationship (SAR) study provides valuable insights for understanding intermolecular interactions between a protein or peptide and other biologically active molecules. In their natural environment, peptides or proteins adopt unique, conformationally-constrained structures in order to recognize and bind to their binding partners, and to form a molecular complex therewith, which in turn elicit particular activities. Examples of protein-protein binding partners include enzyme-substrate, ligand-receptor, and antigen-antibody. Determination of the conformation of a peptide in its native form, therefore, become crucial for closely mimicking its in vivo activity and rationally designing its analogues which may be useful as drugs.

Most small peptides are highly flexible and do not typically adopt unique solution conformations; in particular, they do not maintain the structure that the same sequence adopts in the native protein. The lack of fixed structure reduces the affinity the peptide might have for a target (for entropic reasons) and makes determination of the active conformation of the molecule extremely difficult. Because of this, many strategies have been described to introduce constraints into peptides (such as D-amino acids, disulfide or other crosslinks), or to replace parts of the peptide with more rigid non-peptide scaffolds. Indeed, such peptidomimetics have been widely used to perform structure-activity studies in a systematic way to provide information about the specific amino acid residues or functional groups in a peptide that are adaptable to a particular conformation and are important to biological activities.

Several constrained protein scaffolds, capable of presenting a protein of interest as a conformationally-restricted domain have been identified, including minibody structures (Bianchi et al. (1994) *J Mol Biol* 236:649-659), loops on β-sheet turns, coiled-coil stem structures (Myszka & Chaiken (1994) *Biochem* 33:2363-2372), zinc-finger domains, cysteine-linked (disulfide) structures, transglutaminase linked structures, cyclic peptides, helical barrels or bundles, leucine zipper motifs (Martin et al. (1994) *EMBO J.* 13:5303-5309), and etc. Of the identified protein scaffolds, β-turns have been implicated as an important site for molecular recognition in many biologically active peptides. Smith & Pease (1980) *CRC Crit Rev Biochem* 8:315-300. Consequently, peptides containing conformationally constrained β-turns are particularly desirable. The great majority of the identified β-turn bearing peptides are cyclopeptides which have been generated by the cyclization of a peptide similar to a sequence in the natural substrate. Milner-White (1989) *Trends Pharmacol Sci* 10:70-74. These cyclopeptides, however, may still retain significant flexibility. For this reason, many studies have attempted to introduce rigid, nonpeptide compounds which mimic the β-turn. Peptides with such nonpeptide β-turn mimic provide useful leads for drug discovery. Ball & Alewood (1990) *J Mol Recog* 3:55-64; WO 94/03494 (Kahn).

One of the revolutionary advances in drug discovery is the development of combinatorial libraries. Combinatorial libraries are a collection of different molecules, such as peptides, that can be made synthetically or recombinantly. Combinatorial peptide libraries contain peptides in which all amino acids have been incorporated randomly into certain or all positions of the peptide sequence. Such libraries have been generated and used in various ways to screen for peptide sequences which bind effectively to target molecules and to identify such sequences.

Many methods for generating peptide libraries have been developed and described. For example, members of the peptide library can be created by split-synthesis performed on a solid support such as polystyrene or polyacrylamide resin, as described by Lam et al. (1991) *Nature* 354:82 and PCT publication WO 92/00091. Another method disclosed by Geysen et al., U.S. Pat. No. 4,833,092 involves the synthesis of peptides in a methodical and predetermined fashion, so that the placement of each library member peptide gives information concerning the synthetic structure of that peptide.

Considerable effort has been devoted to introducing structural constraints into combinatorial peptide libraries so that the member peptides represent more closely to their native counterparts. Houston et al. U.S. Pat. No. 5,824,483 describes a synthetic peptide library containing peptides featuring α-helical conformation and thus capable of forming coiled-coil dimers with each other. McBride et al. (1996) *J Mol Biol* 259:819-827 describe a synthetic library of cyclic peptides mimicking the anti-tryptic loop region of an identified proteinase inhibitor.

A complementary method for peptide library-based lead discovery is display of libraries on filamentous bacteriophages. This method allows the preparation of libraries as large as $10^{10}$-$10^{12}$ unique peptide members, many orders of magnitude larger than libraries that may be prepared synthetically. In addition to large library sizes, advantages of phage display include ease of library construction (Kunkel mutagenesis), coupling of the binding entity (displayed peptide) to a unique identifier (its DNA sequence), a selection protocol for amplifying rare binding clones in a pool, and the high fidelity of biosynthesis (compared to synthetic methods). Furthermore, rapid and inexpensive selection protocols are available for identifying those library members that bind to a target of interest. However, only natural peptides composed of L-amino acids may be displayed on phage, so the problem of defining three-dimensional structure-activity relationships is more difficult than it might be for a constrained peptidomimetic containing non-naturally occurring peptides or nonpeptide compounds. One possible solution to this problem is to use the structural constraints of a folded protein to present small variable peptide segments. Indeed, several small, stable proteins have been proposed as peptide display scaffolds. Nygren & Uhlen (1997) *Curr. Opin. Struct. Biol.* 7:463-469; Vita et al. (1998) *Biopolymers* 47:93-100; Vita et al. (1999) *Proc. Natl. Acad. Sci. USA* 96:13091-13096; Smith et al. (1998) *J. Mol. Biol.* 277:317-332; Christmann et al. (1999) *Protein Engng.* 12:797-806. Unfortunately, it is not clear that protein ligands obtained by this approach could be transformed to small-molecule drug leads. Epitope transfer from proteins to small peptides or to non-peptide small molecules remains an extremely challenging problem. Cochran (2000) *Chem. Biol.* 7:R85-R94.

Therefore, despite of extensive studies of the rules governing conformational preferences in natural peptides and the existence of several peptide library systems, those features necessary for structural stability of natural peptides remain poorly understood. In particular, there has been little systematic or quantitative assessment of the effect of residue substitutions and non-covalent interactions on structure.

DISCLOSURE OF INVENTION

The present invention provides a novel model system for assessing individual residue contributions to the stability of a defined peptide scaffold and for evaluating a series of substitutions presented in a combinatorial peptide library. The peptides of the invention are cyclized via disulfide bond between two cysteines within the peptide sequences. Amino acid substitutions at various defined residue sites influence the conformation of the cyclic peptides and their energy stabilities. The invention also provides methods of screening for and analyzing cyclic peptides with a specific secondary structure, β-turn, which provides further structural constraints to the peptides. The subject peptide library comprising a collection of β-turn bearing cyclic peptides can be used in screening for candidate biologically active molecules through molecular binding assays. Methods for such screenings are also provided by the instant invention. The compositions and methods of the invention can be used in analyzing the structure-activity relationships of peptides of interests, thereby providing insightful information for studies of molecular interactions involved in particular biological processes, as well as for rational design of therapeutic agents.

MODE(S) FOR CARRYING OUT THE INVENTION

I. Definitions

Figure 1:
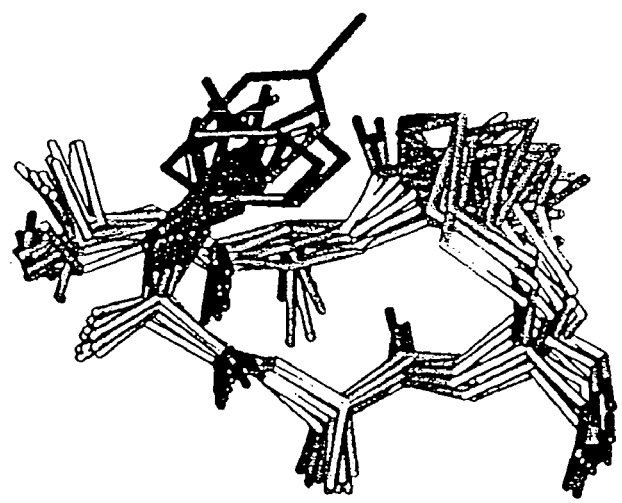
FIG. 1 depicts the design of bhp, a 10-amino acid model β-hairpin peptide. (A) Superimposed structures illustrate packing between disulfides and side chains of the closest non-hydrogen-bonded residues; (B) Schematic representation of the bhp model β-hairpin peptide with the side chains of the non-hydrogen-bonded residues 1, 3, 8 and 10 shown. X represents the varied residue selected from 19 of the 20 natural L-amino acids (excluding Cys).
Figure 1:
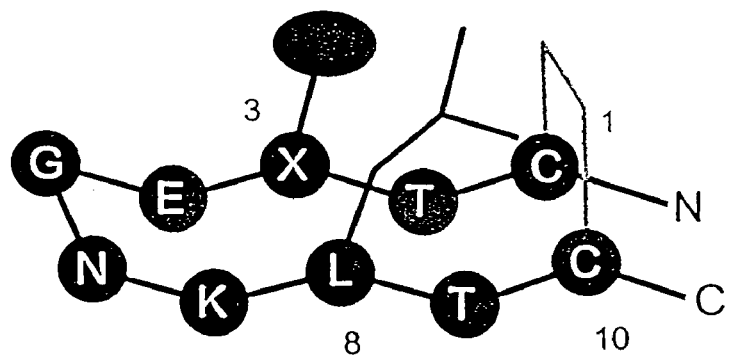
Figure 1:

The term "β-turn" refers to a protein secondary structure consisting of a tetrapeptide sequence which causes the peptide chain to reverse direction, and which often contains a 4' to 1' hydrogen bond, forming a pseudo 10-membered ring. The most widely accepted classification of the different conformations of the β-turn is described in Chou and Fasman (1977) *J Mol Biol* 115:135-175, the disclosure of which is expressly incorporated by reference herein. Various β-turn types have been defined, including for example, type I, I', II, and II'. For the purpose of this invention, the term "reverse-turn" is used in a general sense to encompass well known protein secondary structures including β-turns, γ-turns, β-hairpins and β-bulges.

"Cell," "cell line," and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The terms "competent cells" and "electoporation competent cells" mean cells which are in a state of competence and able to take up DNAs from a variety of sources. The state may be transient or permanent. Electroporation competent cells are able to take up DNA during electroporation.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein or may be a minor coat protein. A "major" coat protein is a coat protein which is present in the viral coat at 10 copies of the protein or more. A major coat protein may be present in tens, hundreds or even thousands of copies per virion.

The terms "electroporation" and "electroporating" mean a process in which foreign matter (protein, nucleic acid, etc.) is introduced into a cell by applying a voltage to the cell under conditions sufficient to allow uptake of the foreign matter into the cell. The foreign matter is typically DNA.

A "fusion protein" is a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from a mammal or plant. The DNA may, optionally, include selection genes, for example, antibiotic resistance genes, temperature resistance genes, etc.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA may be treated in a suitable buffer for at least 15 minutes at 15° C. with about 10 units of the Klenow fragment of DNA polymerase I or T4 DNA polymerase in the presence of the four deoxyribonucleotide triphosphates. The DNA may then purified by phenol-chloroform extraction and ethanol precipitation. The DNA fragments that are to be ligated together are put in solution in about equimolar amounts. The solution will generally also contain ATP, ligase buffer, and a ligase such as T4 DNA ligase at about 10 units per 0.5 μg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to a coat protein on the surface of phage, e.g. filamentous phage particles. A utility of phage display lies in the fact that large libraries of randomized protein variants can be rapidly and efficiently sorted for those sequences that bind to a target molecule with high affinity. Display of peptides and proteins libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) *Curr. Opin. Struct. Biol B*:355-362 and references cited therein. In monovalent phage display, a protein or peptide library is fused to a gene III or a portion thereof and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) *Methods: A companion to Methods in Enzymology* 3:205-216. In phage display, the phenotype of the phage particle, including the displayed polypeptide, corresponds to the genotype inside the phage particle, the DNA enclosed by the phage coat proteins.

A "phagemid" is a plasmid vector having a bacterial origin of replication, e.g., ColE1, and a copy of an intergenic region of a bacteriophage. The phagemid may be based on any known bacteriophage, including filamentous bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle. Sambrook et al. 4.17.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, a lambdoid phage, such as lambda, 21, phi80, phi81, 82, 424, 434, etc., or a derivative thereof, a Baculovirus or a derivative thereof, a T4 phage or a derivative thereof, a T7 phage virus or a derivative thereof.

"Preparation" of DNA from cells means isolating the plasmid DNA from a culture of the host cells. Commonly used methods for DNA preparation are the large- and small-scale plasmid preparations described in sections 1.25-1.33 of Sambrook et al. After preparation of the DNA, it can be purified by methods well known in the art such as that described in section 1.40 of Sambrook et al.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published 4 May 1988, or via deoxynucleoside H-phosphonate intermediates as described by Froehler et al. (1986) *Nucl. Acids Res.,* 14:5399-5407). Further methods include the polymerase chain reaction defined below and other autoprimer methods and oligonucleotide syntheses on solid supports. All of these methods are described in Engels et al. (1989) *Agnew. Chem. Int. Ed. Engl.* 28:716-734. These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides are then purified on polyacrylamide gels.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263 Erlich, ed., *PCR Technology*, (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

DNA is "purified" when the DNA is separated from non-nucleic acid impurities. The impurities may be polar, non-polar, ionic, etc.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (1981) *Nucleic Acids Res.,* 9:6103-6114, and Goeddel et al. (1980) *Nucleic Acids Res.,* 8:4057.

A "transcription regulatory element" will contain one or more of the following components: an enhancer element, a promoter, an operator sequence, a repressor gene, and a transcription termination sequence. These components are well known in the art. U.S. Pat. No. 5,667,780.

A "transformant" is a cell which has taken up and maintained DNA as evidenced by the expression of a phenotype associated with the DNA (e.g., antibiotic resistance conferred by a protein encoded by the DNA).

"Transformation" or "transforming" means a process whereby a cell takes up DNA and becomes a "transformant". The DNA uptake may be permanent or transient.

A "variant" or "mutant" of a starting polypeptide, such as a fusion protein or a heterologous polypeptide (heterologous to a phage), is a polypeptide that 1) has an amino acid sequence different from that of the starting polypeptide and 2) was derived from the starting polypeptide through either natural or artificial (manmade) mutagenesis. Such variants include, for example, deletions from, and/or insertions into and/or substitutions of, residues within the amino acid sequence of the polypeptide of interest. Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference.

The term "peptide analog" refers to a molecule or part thereof which is comprised of amino acids and resembles, with regard to its binding ability and/or specificity, a specific molecule, as defined above. Such peptide analogs may be found or constructed by protein engineering techniques, such methods being well known to those of skill in the art. Alternatively, such peptide analogs may be found by a reiterative screening process, for example wherein a natural binding partner of the specific molecule (which specific molecule is not necessarily a protein or peptide), or a portion thereof, is used as described herein (i.e. in a chimeric protein) to screen peptide compounds for the ability to bind to it. In a second screening step, the newly found peptide compound (or a portion thereof) may itself be used as a peptide analog of the specific molecule in a chimeric protein to screen for analogs of the natural binding partner. Other methods for finding or making peptide analogs will be apparent to those of skill in the art.

The term "epitope" means an antigen or portion thereof which is capable of binding with an antibody as an antigenic determinant.

By "binding partner complex" is meant the association of two or more molecules which are bound to each other in a specific, detectable manner; thus the association of ligand and receptor, antibody and antigen, and chimeric protein and the compound to which it binds.

The term "directly or indirectly labeled" refers to a molecule may contain a label moiety which moiety emits a signal which is capable of being detected, such as a radioisotope, a dye, or a fluorescent or chemiluminescent moiety, or may contain a moiety, such as an attached enzyme, ligand such as biotin, enzyme substrate, epitope, or nucleotide sequence which is not itself detected but which, through some additional reaction, is capable of indicating the presence of the compound.

By "ligand" is meant a molecule or a multimeric molecular complex which is able to specifically bind another given molecule or molecular complex. Often, though not necessarily, a ligand is soluble while its target is immobilized, such as by an anchor domain imbedded into a cell membrane.

The term "receptor" refers to at least a portion of a molecule, or a multimeric molecular complex which has an anchor domain embedded into a cell membrane and is able to bind a given molecule or molecular complex. Many receptors have particularly high affinity for a ligand when either or both the receptor or ligand are in a homo- or hetero multimeric form, such as a dimer.

The term "solid support" refers to an insoluble matrix either biological in nature, such as, without limitation, a cell or bacteriophage particle, or synthetic, such as, without limitation, an acrylamide derivative, cellulose, nylon, silica, and magnetized particles, to which soluble molecules may be linked or joined.

By "naturally-occurring" is meant normally found in nature. Although a chemical entity may be naturally occurring in general, it need not be made or derived from natural sources in any specific instance.

By "non naturally-occurring" is meant rarely or never found in nature and/or made using organic synthetic methods.

"Modified" means non naturally-occurring or altered in a way that deviates from naturally-occurring compounds.

II. General

The present invention is directed to conformationally-constrained peptides and peptide libraries that are useful for structure-activity analysis of bioactive molecules and for drug lead discovery. The peptide of the invention comprises two Cysteine residues that are capable of forming disulfide bond with each other. Thus, the peptide adopts a cyclic form in solution, which facilitates the formation of a β-hairpin scaffold. Disulfide cyclization is helpful, although not sufficient to constrain the structure of many peptides. The rest of the residues of the peptide are further selected to be significantly biased toward the formation of the hairpin structure. Moreover, a subset of the residues within the peptide of the invention is varied to provide relative diversity for mimicking various bioactive peptides having a identified secondary structure, such as β-turn, which has been proven significant in biological processes.

In one aspect, the invention encompasses a peptide library comprising a collection of structurally constrained peptides. Each peptide member of the library comprises amino acid sequence C1-A1-A2-(A3)$_n$-A4-A5-C2 (SEQ ID NO:1), wherein A1, A2, A3, A4, and A5 are naturally occurring L-amino acids;

the amino terminus of Cysteine C1 is optionally protected with a amino protecting group;

the carboxy terminus of Cysteine C2 is optionally protected with carboxy protecting group;

A1 and A5 are selected from the group consisting of amino acids W, Y, F, H, I, V and T;

A2 and A4 are selected from the group consisting of amino acids W, Y, F, L, M, I, and V;

A3 is any naturally occurring L-amino acid and n is an integer that is selected from the group consisting of 3, 4, 5, 6, 7, 8, 9, 10, 11 and 12; and C1 and C2 are joined together by a disulfide bond thereby forming a cyclic peptide.

In one preferred embodiment, the peptides of the invention have a β-branched residue having two non-hydrogen substituents on the β-carbon of the amino acid residue at position A1 or A5 or both. More preferably, A1 or A5 is threonine (T). Even more preferably, both A1 and A5 are threonine residues.

According to another preferred embodiment, the peptides have an aromatic residue W, Y, F or H at position A1 or A5 or both. More preferably, A1 or A5 is W. Additional preferred peptides of the invention have a branched aliphatic residue I, V or T at A1, A5 or both.

In another preferred embodiment, the peptides of the invention have an aromatic residue W, Y or F at position A2 or A4 or both. More preferably, A2 or A4 is W; and even more preferably, A2 and A4 are Ws. Another preferred embodiment include peptides having an unbranched aliphatic residue L or M at position A2 or A4 or both; more preferably A2 or A4 is Leucine. Still other preferred peptides have a branched aliphatic residue I or V at position A2 or A4 or both.

In the peptides of the invention, the number of the A3 residues n can be 3, 4, 5, 6, 7, 8, 9, 10, 11, or 12; preferably 4, 5, 6, 7, 8, 9, or 10; and more preferably 4, 5, or 6. In one embodiment, n is 4 and the resulting peptides are decamers. In these decamers, the residue sites A1, A2, A4 and A5 are each from a selected group of amino acid residues as described above, whereas the middle (A3)$_4$ is a tetrapeptide sequence with varying amino acids. In one aspect of the invention, the (A3)$_4$ tetrapeptide sequence is selected from those favorable to forming a β-turn structure, including but not limited to EGNK [SEQ ID NO: 44], ENGK [SEQ ID NO: 45], QGSF [SEQ ID NO: 46], VWQL [SEQ ID NO: 47], and GPLT [SEQ ID NO: 48].

In one aspect, the library of the instant invention contains at least about $10^2$ member peptides, each of which has at least one amino acid variation from others. Preferably, the library contains at least about $10^4$ peptides, more preferably about $10^{10}$ peptides and even more preferably at least about $10^{12}$ peptides. According to various embodiments, the amino acid variation occurs at defined positions within the peptides. For example, variations can occur at non hydrogen-bonded (NHB) strand sites (e.g., A1/A5) or hydrogen-bonded strand sites (e.g., A2/A4); a residue and its crqss-strand counterpart (e.g., A1/A5 or A2/A4) can have same or different amino acids. Variations can also occur at the middle (A3)$_n$ sites, wherein A3 can be any of the 20 naturally occurring L-amino acids.

The carboxy terminal end and the amino terminal end of the cyclic peptide may be protected with any known protecting groups or may be bonded to other amino acid residues (generally naturally occurring residues), both in the (L) and in the (D) form through conventional amide peptide bonds. One embodiment of the present invention comprises the peptide X$_n$-C$_1$-A1-A2-(A3)$_n$-A4-A5-C2-X$_n$, wherein C1 and C2 are cysteines: A1, A2, A3, A4, and A5 are naturally occurring L-amino acids; A1 and A5 are independently amino acids W, Y, F, H, I, V, or T; A2 and A4 are independently amino acid W; A3 is any naturally occurring L-amino acid and n is an integer that is 3, 4, 5, 6, 7, 8, 9, 10, 11, or 12: X consists of any naturally occurring amino acid and n is any integer from 1 to about 50; and C1 and C2 together form a disulfide bond thereby forming a cyclic peptide; the amino terminus of C1 is optionally protected with an amino protecting group; and the carboxy terminus of C2 is optionally protected with a carboxy protecting group [SEQ ID NO: 49]. The protecting groups and additional residues can be added using conventional peptide synthesis techniques. Generally from 1 to about 50, preferably from 1 to about 20, amino acid residues may be present on each of the carboxy and amino terminal positions, independently. These additional residues may be part of a known protein containing a beta turn of interest or may be any other desired sequence of residues. These additional residues may be added to determine the effect of the beta turn structure on the structure of the overall polypeptide or to determine the effect of the additional residues on the binding of the beta turn cyclic peptide with a protein of interest.

Alternatively, a library of cyclic peptides of the invention can be prepared in which one or more of residues A1, A2, A4, and/or A5 are independently fixed and residues A3 are varied using known methods of generating peptide libraries.

A preferred method of generating a library is phage display. Any known method of phage display, such as those discussed in more detail below, may be used in the method of the invention.

In one embodiment of the invention, the cyclic peptide of the invention is fused to at least a portion of a phage coat protein to form a fusion protein containing the cyclic peptide of the invention. The fusion protein can be made by expressing a gene fusion encoding the fusion protein using known techniques of phage display such as those described below. The fusion protein may form part of a phage or phagemid particle in which one or more copies of the cyclic peptide are displayed on the surface of the particle. A gene comprising a nucleic acid encoding the cyclic peptide or the fusion protein are within the scope of the invention.

The present invention also encompasses methods of screening for peptides having a β-hairpin scaffold that is conformationally stabilized, comprising the steps of a) providing a combinatorial library of the invention as described above; b) selecting at least two peptides from the combinatorial library, wherein said at least two peptides differ by one amino acid at a particular position A1, A2, A3, A4 or A5; c) determining the conformations of the peptides; d) measuring and comparing the relative stabilities of the peptides; and e) selecting the peptide having a conformationally stabilized β-hairpin scaffold. The conformation and stability of the peptides can be determined using many methods known in the art such as NMR, molecular modeling, crystallography and free energy calculation. See, for example, Cavanagh et al. (1995) *Protein NMR Spectroscopy, Principles and Practices* (Academic Press, San Diego). Particular methods of determining peptide conformation and stability are described in more detail below by way of examples. The β-turn containing peptides of the invention can be useful for mimicking native bioactive proteins in their binding activities.

The identity of the β-turn residues A3 may be determined by studying known protein structures and then substituting the known structural sequence into the structured beta hairpin compound of the invention. In this embodiment, residues A3 are taken from the known protein whereas residues A1, A2, A4 and A5 are as described for the invention. In this way, the fixed residues of invention can be used to structure particular turns from proteins of interest, allowing one to test whether the protein turn is sufficient for binding to a known protein binding partner, or for antagonizing the relevant protein-protein interaction.

The invention also includes methods of identifying a peptide capable of binding a specific binding partner, comprising the steps of a) providing a combinatorial library as described above; b) contacting the combinatorial library with a binding partner; c) selecting from the library peptides capable forming a noncovalent complex with the binding partner; and d) optionally isolating said peptides of step. Methods and technologies for assessing peptide binding activity and isolating peptides of interest are known in the art and described in more detail below.

Binding partners of the peptides of the invention can be at least a portion of any molecules, including any known or unknown peptides, proteins, other macromolecules or chemical compounds that are capable of binding to the peptides and optionally exerting bioactivities. Protein molecules such as receptors, ligands, antigens, antibodies, enzymes and enzyme substrates and fragments or portions thereof are encompassed by "binding partners." Other non-protein chemical compounds, organic or inorganic, can also be the binding partners of the peptides.

III. β-Hairpin Peptides

One embodiment of the present invention involves short peptides that adopt β-hairpin conformations in solution. The component parts of β-hairpin structure include paired antiparallel β-strands and, preferably, β-turns. The preferential placement of disulfide-bonded cysteine pairs at non-hydrogen bonded sites in the β-strands have been studied, as are specific pairs of cross-strand residues that are statistically favored (in either hydrogen bonded or non-hydrogen bonded sites), at least in proteins. One study describes experimental stability measurements of mutant proteins in which various pairs of residues have been introduced into hydrogen bonded sites on adjacent antiparallel strands. Smith & Regan (1995) *Science* 270: 980-982. Attempts have been made to determine intrinsic preferences for individual amino acids to adopt conformations suited to the geometry of a β-strand, either by analyzing the residue content of β-strands (Chou & Fassman (1978) *Annu. Rev. Biochem.* 47:251-276) or by substituting various amino acids into a P-strand of a protein and measuring the relative stabilities of the mutants (Kim & Berg (1993) *Nature* 362:267-270; Minor & Kim (1994) *Nature* 367:660-663; Minor & Kim (1993) *Nature* 371:264-267; Smith et al. *Biochemistry* (1994) 33:5510-5517). A revised statistical method for assigning residue conformations has improved correlation with the various experimental propensity scales (Munoz & Serrano (1994) Proteins 20:301-311). The propensity assigned to tryptophan is moderate in all reported scales.

It has recently been shown that for some short, linear peptides (4-16 amino acids), the hairpin conformation is partially populated in aqueous solution. Both designed peptides and peptides taken from protein sequences have exhibited this behavior. In general, these studies involve peptides with statistically strong turn sequences (e.g., asn-gly at i+1, i+2). Nevertheless, hairpin populations seldom exceed 40-50% in aqueous solution.

A 16-mer peptide derived from the protein ubiquitin but with a statistically more common turn sequence (MQIGVKNPDGTITLEV (SEQ ID NO: 41)) did form a highly populated hairpin in water (ca. 80%), but the hairpin did not have the same strand register as in the native protein (Searle et al. (1995) *Nat. Struct. Biol.* 2:999-1006). Another group studied a similar peptide in which the turn region was replaced with several sequences (MQIGVKSXXKTITLKV (SEQ ID NO: 42)), wherein XX=pro-ala or pro-gly; Haque & Gellman (1997) *J. Am. Chem. Soc.* 119:2303-2304). Evidence for the hairpin structure, with native strand register, was observed for turns containing D-amino acids but not for L-amino acid sequences. No population estimates were given in this study.

Several groups have studied model peptides based originally on a sequence from the protein tendamistat. The peptide YQNPDGSQA (SEQ ID NO: 26) shows NMR evidence of a small population of hairpin in water (Blanco et al. (1993) *J. Am. Chem. Soc.* 115:5887-5888; de Alba et al. (1995) *Eur. J. Biochem* 233:283-292; Constantine et al. (1995) *J. Am. Chem. Soc.* 117:10841-10854; Friedrichs et al. *J. Am. Chem. Soc.* (1995) v 117, pp. 10855-10864). A variant of this peptide with strand residues of higher expected β-propensity (IYSNPDGTWT (SEQ ID NO: 27)) was compared to a second peptide with a different turn sequence (IYSNSDGTWT (SEQ ID NO: 28)). Both peptides were estimated by NMR as 30% hairpin in water (de Alba et al. (1996) *Fold. Des.* 1: 133-144). Further variation of this peptide, predominantly in the turn sequence, yielded hairpins of various structures and mixed populations. Generally no one conformer population exceeded 50% (de Alba et al.

(1997) *J. Am. Chem. Soc.* 119:175-183). In a final study, the three N-terminal residues in peptide ITSNSDGTWT (SEQ ID NO: 29)) were replaced with various sequences. Again, mixed conformers were frequently observed and populations of a given hairpin conformer were generally less than 50%: one peptide (YITNSDGTWT (SEQ ID NO: 30)) did form a register-shifted hairpin that was highly populated (80%; de Alba et al. (1997) *Protein Sci.* 6:2548-2560). The authors of these studies conclude that conformational preferences of the turn residues dominate cross-strand interactions in determining the stability of hairpins, at least in these short model peptides.

Analysis of hairpin sequences in crystal structures has allowed the design of a different series of β-hairpin peptides. The target structure was a type I' turn flanked by three-residue strands. Arg-gly sequences were added to the ends to improve stability. The peptide RGITVNGKTYGR (SEQ ID NO: 31) is partially folded into a hairpin conformation (about 30%) as determined by NMR (Ramirez-Alvarado et al. (1996) *Nat. Struct. Biol.* 3:604-612). The importance of strand residues is indicated by replacement of the ile and val, the lys and tyr, or all four residues with alanine. None of the alanine-substituted peptides showed any tendency to form a hairpin. The same authors reported a second series of experiments in which position i+1 of the turn was varied (asn to asp, ala, gly or ser). No peptide was more structured than the original sequence with asn in the turn (Ramirez-Alvarado et al. (1997) *J. Mol. Biol.* 273:898-912). A review describing this work stated that adding glu-lys pairs to the termini of the model peptide stabilized the hairpin but did not give further details (Ramirez-Alvarado et al. (1999) *Bioorg. Med. Chem.* 7:93-103).

Another model peptide series (RYVEVXGOrnKILQ (SEQ ID NO: 32)) has yielded evidence for hairpin formation in water. Residue X as D-pro or L-asn yields characteristic NOEs and alpha-H shifts, but the L-pro peptide is unfolded. No population estimates are given, but D-pro appears to give the more stable hairpin (Stanger & Gellman (1998) *J. Am. Chem. Soc.* 120:4236-4237).

A designed 16-residue peptide (KKYTVSINGKKITVSI (SEQ ID NO: 33)) based on the met repressor DNA binding region formed a hairpin structure in water with an estimated population at 50% at 303 K. Truncation of one strand showed that the turn was populated without the strand interactions, although to a lesser degree (35%). An analysis of the thermodynamic parameters for hairpin formation showed that folding is enthalpically unfavored and entropically driven, with $\Delta G=0.08$ kcal/mol at 298 K (Maynard & Searle (1997) *Chem. Commun.* 1297-1298; Griffiths-Jones et al. (1998) *Chem. Commun.* 789-790; Maynard et al. (1998) *J. Am. Chem. Soc.* 120:1996-2007).

A final hairpin peptide (GEWTYDDATKTFTVTE (SEQ ID NO: 34)) derived from the B1 domain of protein G (GB1) has some features relevant to the peptides of the invention. Unlike the above described model hairpins, the GB1 hairpin has four threonine residues at hydrogen-bonded sites in the strands, including one thr-thr cross-strand pair. This is generally believed to be an unfavorable pairing. In addition, there are trp-val and tyr-phe pairs at adjacent nonhydrogen-bonded sites that might interact to form a small hydrophobic core. The reported data indicate that the GB1 peptide formed a well-populated hairpin (about 50%) in water. The data are consistent with native strand pairing (Blanco et al. (1994) *Nat. Struct. Biol.* 1:584-590). A denaturation study of the GB1 peptide allowed estimation of 80% hairpin at 273 K, and analysis of the data (assuming $\Delta Cp=0$) yielded $\Delta H=-11.6$ kcal/mol, $\Delta S=-39$ cal/mol K: i.e., folding is enthalpically driven and entropically disfavored (Munoz et al. *Nature* (1998) v 390, pp. 196-199). The relative roles of enthalpy and entropy are reversed compared to the met repressor peptide described above.

Several designed three-stranded sheets have been reported: one of these contains only the usual 20 amino acids occurring in proteins and folds in water (Kortemme et al. (1998) *Science* 281:253-256). One aspect of the design is addition of a trp at a nonhydrogen-bonded position (by analogy to WW domains) while also changing two nonhydrogen-bonded residues on the next strand to unbranched amino acids. The authors state that the branched residues would not allow the trp side chain to pack across to the next strand. Thermodynamic analysis of denaturation data yields a folding free energy of –0.6 kcal/mol at 278 K (estimated folded population=80-90%).

Numerous examples have been reported of disulfide-constrained peptides intended to mimic protein hairpins or as de novo designed hairpins. In many cases the designs include D-cysteines at one or both ends, as it was initially thought that disulfide bond geometry was not compatible with the cross-strand geometry of hairpins. However, there are some examples that do use L-cys.

Evidence for structure is lacking in most studies of disulfide-cyclized peptides. Examples listed here are those that have been experimentally determined, or that use no unusual amino acids and have potency close to a larger, hairpin-containing protein in a biological assay.

The structure of a hexapeptide (Boc-CL-Aib-AVC-NMe) was determined crystallographically, revealing a type II' turn and β-sheet geometry (Karle et al. *J. Am. Chem. Soc.* (1988) v 110, pp 1958-1963). An octapeptide with the same cysteine spacing (ACSPGHCE (SEQ ID NO: 35)) was studied by NMR, and has a similar structure with a turn centered on pro-gly (Walse et al. (1996) *J. Comput.-Aided Mol. Des.* 10:11-22). Peptides of the form Ac-CXPGXC-NHMe (SEQ ID NO: 43) were evaluated by measurement of disulfide exchange equilibria, which indicated turn preferences between peptides of as much as 1 kcal/mol (Milburn et al. (1987) *J. Am. Chem. Soc.* 109:4486-4496).

An eleven-residue cyclic peptide (CGVSRQGKPYC (SEQ ID NO: 36)) based on the gene 5 protein from M13 is stably structured in aqueous solution, as demonstrated by NMR analysis. The cyclic peptide adopts a structure that is quite similar to the corresponding protein loop. The authors claim that well-defined β-hairpin structure had not been previously reported for any unprotected disulfide-constructed cycle (Rietman et al. (1996) *Eur. J. Biochem* 238: 706-713). This peptide has a val-pro pair at the nonhydrogen bonded sites nearest to the cysteines.

Cyclization of peptides corresponding to loops from Linulus anti-lipopolysaccharide factor (LALF) based on X-ray structure yielded potent lipid A binders. There is no evidence for structure in these peptides. Several of the peptides have aromatic-aromatic pairs at the nonhydrogen-bonded sites nearest the cysteines; however, the most potent (GCKPT-FRRLKWKYKCG (SEQ ID NO:37)) has a pro-tyr pair (Ried et al. (1996) *J. Am. Chem. Soc.* 271:28120-28127).

Disulfide-cyclized peptides from the hairpin region of a rabbit defensin have antibacterial activity exceeding (about 5 to 10-fold) that of the linear analogs. Circular dichroism spectroscopy indicates some non-random structure in phosphate buffer. The more potent peptide (CAGFMRIRGRIH-PLCMRR (SEQ ID NO: 38)) has a gly-pro pair at the nonhydrogen bonded sites nearest to the cysteines (Thennarasu & Nagaraj (1999) *Biochem. Biophys. Res. Commun.* 254:281-283).

A final study describes several peptides from the loops of domain 1 of human CD4. In addition to a disulfide constraint, the authors have added exocyclic aromatic amino acids to the peptide termini. For example, a peptide covering CD4 residues 39-44 was constrained as FCNQGSFLCY (SEQ ID NO: 39). No evidence for structure is given, but one cyclic peptide (FCYICEVEDQCY (SEQ ID NO: 40)) was reported to antagonize both normal CD4 interactions and those involved in CD4-mediated cell entry by HIV (Zhang et al. (1996) *Nature Biotechnology* 14:472-475; Zhang et al. (1997) *Nature Biotechnology* 15:150-154).

IV. Peptide Libraries

Many methods for generating peptide libraries that are known in the art can be used to generate the libraries of the invention. In one embodiment, members of the peptide library can be created by split-synthesis performed on a solid support such as polystyrene or polyacrylamide resin, as described by Lam et al. (1991) *Nature* 354:82 and PCT publication WO 92/00091. In one aspect of the invention, the library of cyclic peptides can be prepared in which one or more of residues A1, A2, A4, and/or A5 are independently fixed and residues A3 are varied.

A preferred method of generating the library of the present invention is phage display. In a phage display library, the cyclic peptide of the invention is fused to at least a portion of a phage coat protein to form a fusion protein. The fusion protein can be made by expressing a gene fusion encoding the fusion protein using known techniques of phage display such as those described below. The fusion protein may form part of a phage or phagemid particle in which one or more copies of the cyclic peptide are displayed on the surface of the particle. A gene comprising a nucleic acid encoding the cyclic peptide or the fusion protein are within the scope of the invention.

In another embodiment, the invention is a method comprising the steps of constructing a library containing a plurality of replicable expression vectors, each expression vector comprising a transcription regulatory element operably linked to a gene fusion encoding a fusion protein, wherein the gene fusion comprises a first gene encoding a cyclic peptide of the invention and a second gene encoding at least a portion of a phage coat protein, where the library comprises a plurality of genes encoding variant cyclic peptide fusion proteins. Variant first genes and libraries thereof encoding variant cyclic peptides are prepared using known mutagenesis techniques described in more detail below.

The invention also includes expression vectors comprising the fusion genes noted above, as well as a library of these vectors. The library of vectors may be in the form of a DNA library, a library of virus (phage or phagemid) particles containing the library of fusion genes or in the form of a library of host cells containing a library of the expression vectors or virus particles.

Also within the invention is a method of selecting novel binding polypeptides comprising (a) constructing a library of variant replicable expression vectors comprising a transcription regulatory element operably linked to a gene fusion encoding a fusion protein wherein the gene fusion comprises a first gene encoding the cyclic peptide of the invention, and a second gene encoding at least a portion of a phage coat protein, where the variant expression vectors comprise variant first genes; (b) transforming suitable host cells with the vectors; (c) culturing the transformed host cells under conditions suitable for forming recombinant phage or phagemid virus particles containing at least a portion of the expression vector and capable of transforming the host, so that the particles display one or more copies of the fusion protein on the surface of the particle; (d) contacting the particles with a target molecule so that at least a portion of the particles bind to the target molecule; and (e) separating the particles that bind from those that do not. In the method of the invention, the phage coat protein is preferably the gene III or gene VIII coat protein of a filamentous phage such as M13. Further, preferably the culturing of the transformed host cells is under conditions suitable for forming recombinant phage or phagemid particles where the conditions are adjusted so that no more than a minor amount of phage or phagemid particles display one or more copies of the fusion protein on the surface of the particle (monovalent display).

The invention also includes a method of introducing structural bias into a phage-displayed library, using steps (a) through (e) described above. The invention further includes a method of selecting beta hairpin forming peptide structures from a phage-displayed library, using steps (a) through (e) described above where the target is known to bind beta hairpin peptide structures, preferably a protein target known to so bind.

Bacteriophage (phage) display is a known technique by which variant polypeptides are displayed as fusion proteins to the coat protein on the surface of bacteriophage particles (Scott, J. K. and Smith, G. P. (1990) *Science* 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla et al. (1990) *Proc. Natl. Acad. Sci. USA* 87:6378) or protein (Lowman et al. (1991) *Biochemistry* 30:10832; Clackson et al. (1991) *Nature* 352: 624; Marks et al. (1991), *J. Mol. Biol.* 222:581; Kang et al. (1991) *Proc. Natl. Acad. Sci. USA* 88:8363) libraries on phage have been used for screening millions of polypeptides for ones with specific binding properties (Smith, G. P. (1991) *Current Opin. Biotechnol.* 2:668). Sorting phage libraries of random mutants requires a strategy for constructing and propagating a large number of variants, a procedure for affinity purification using the target receptor, and a means of evaluating the results of binding enrichments. U.S. Pat. No. 5,223,409; U.S. Pat. No. 5,403,484; U.S. Pat. No. 5,571,689; U.S. Pat. No. 5,663,143.

Typically, variant polypeptides, such as the cyclic compounds of the invention, are fused to a gene III protein, which is displayed at one end of the virion. Alternatively, the variant polypeptides may be fused to the gene VIII protein, which is the major coat protein of the virion. Such polyvalent display libraries are constructed by replacing the phage gene III with a cDNA encoding the foreign sequence fused to the amino terminus of the gene III protein.

Monovalent phage display is a process in which a protein or peptide sequence is fused to a portion of a gene III protein and expressed at low levels in the presence of wild-type gene III protein so that particles display mostly wild-type gene III protein and one copy or none of the fusion protein (Bass et al. (1990) *Proteins* 8:309; Lowman, H. B. and Wells, J. A. (1991) *Methods: a Companion to Methods in Enzymology* 3:205). Monovalent display has the advantage over polyvalent phage display that progeny phagemid particles retain full infectivity. Avidity effects are reduced so that sorting is on the basis of intrinsic ligand affinity, and phagemid vectors, which simplify DNA manipulations, are used. See also U.S. Pat. No. 5,750,373 and U.S. Pat. No. 5,780,279. Others have also used phagemids to display proteins, particularly antibodies. U.S. Pat. No. 5,667,988; U.S. Pat. No. 5,759,817; U.S. Pat. No. 5,770,356; and U.S. Pat. No. 5,658,727.

Methods of generating peptide libraries and screening these libraries are also disclosed in U.S. Pat. No. 5,723,286; U.S. Pat. No. 5,432,018; U.S. Pat. No. 5,580,717; U.S. Pat. No. 5,427,908; and U.S. Pat. No. 5,498,530. See also U.S. Pat. No. 5,770,434; U.S. Pat. No. 5,734,018; U.S. Pat. No. 5,698,426; U.S. Pat. No. 5,763,192; and U.S. Pat. No. 5,723,323.

A two-step approach may be used to select high affinity ligands from peptide libraries displayed on M13 phage. Low affinity leads are first selected from naive, polyvalent libraries displayed on the major coat protein (protein VIII). The low affinity selectants are subsequently transferred to the gene III minor coat protein and matured to high affinity in a monovalent format.

Although most phage display methods have used filamentous phage, lambdoid phage display systems (WO 95/34683; U.S. Pat. No. 5,627,024), T4 phage display systems (Ren et al. (1998) *Gene* 215:439; Zhu (1997) *CAN* 33:534; Jiang et al. (1997) *CAN* 128:44380; Ren et al. (1997) *CAN* 127: 215644; Ren (1996) *Protein Sci.* 5:1833; Efimov et al. (1995) *Virus Genes* 10:173) and T7 phage display systems (Smith & Scott (1993) *Methods in Enzymology* 217:228-257; U.S. Pat. No. 5,766,905) are also known and can be used to create a library of the cyclic peptides of the invention.

Suitable gene III vectors for display of cyclic peptides of the invention include fUSE5 (Scott, J. K., and Smith G. P. (1990) *Science* 249:386-390); fAFF1 (Cwirla et al. (1990). *Proc. Natl. Acad. Sci. U.S.A.* 87:6378-6382); fd-CAT1 (McCafferty et al. (1990) *Nature (London)* 348:552-554); m663 (Fowlkes et al. (1992) *Biotechniques* 13:422-427); fdtet-DOG, pHEN1 (Roogenboom et al. (1991) *Nucleic Acids Res.* 19:4133-4137); pComb3 (Gram et al. (1992) *Proc. Natl. Acad. Sci. U.S.A.* 89:3576-3580); pCANTAB 5E (Pharmacia); and LamdaSurfZap (Hogrefe (1993) *Gene* 137:85-91).

Phage display methods for proteins, peptides and mutated variants thereof, including constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, contacting the recombinant phage particles with a target molecule so that at least a portion of the particle bind to the target, separating the particles which bind from those that do not bind, are known and may be used with the method of the invention. See U.S. Pat. No. 5,750,373; WO 97/09446; U.S. Pat. No. 5,514,548; U.S. Pat. No. 5,498,538; U.S. Pat. No. 5,516,637; U.S. Pat. No. 5,432,018; WO 96/22393; U.S. Pat. No. 5,658,727; U.S. Pat. No. 5,627,024; WO 97/29185; O'Boyle et al. (1997) *Virology* 236:338-347; Soumillion et al. (1994) *Appl. Biochem. Biotech.* 47:175-190; O'Neil and Hoess. (1995) *Curr. Opin. Struct. Biol.* 5:443-449; Makowski (1993) *Gene* 128:5-11; Dunn (1996) *Curr. Opin. Struct. Biol.* 7:547-553; Choo and Klug (1995) *Curr. Opin. Struct. Biol.* 6:431-436; Bradbury & Cattaneo (1995) *TINS* 18:242-249; Cortese et al., (1995) *Curr. Opin. Struct. Biol.* 6:73-80; Allen et al. (1995) *TIBS* 20:509-516; Lindquist & Naderi (1995) *FEMS Micro. Rev.* 17:33-39; Clarkson & Wells (1994) *Tibtech.* 12:173-184; Barbas 3) *Curr. Opin. Biol.* 4:526-530; McGregor (1996) *Mol. Biotech.* 6:155-162; Cortese et al. (1996) *Curr. Opin. Biol.* 7:616-621; McLafferty et al. (1993) *Gene* 128:29-36.

The gene encoding the coat protein of the phage and the gene encoding the desired cyclic polypeptide portion of the fusion protein of the invention (i.e., the cyclic peptide of the invention fused to at least a portion of a phage coat protein) can be obtained by methods known in the art (see generally, Sambrook et al.). The DNA encoding the gene may be chemically synthesized (Merrfield (1963) *J. Am. Chem. Soc.* 85 :2149) and then mutated to prepare a library of variants as described below.

To ligate DNA fragments together to form a functional vector containing the gene fusion, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15° C. with 10 units of the Klenow fragment of DNA polymerase I (Klenow) in the presence of the four deoxynucleotide triphosphates. The DNA is then purified by phenol-chloroform extraction and ethanol precipitation or other DNA purification technique.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30-6.33 of Sambrook et al.

The DNA fragments that are to be ligated together (previously digested with the appropriate restriction enzymes such that the ends of each fragment to be ligated are compatible) are put in solution in about equimolar amounts. The solution will also contain ATP, ligase buffer and a ligase such as T4 DNA ligase at about 10 units per 0.5 μg of DNA. If the DNA fragment is to be ligated into a vector, the vector is at first linearized by cutting with the appropriate restriction endonuclease(s). The linearized vector is then treated with alkaline phosphatase or calf intestinal phosphatase. The phosphatasing prevents self-ligation of the vector during the ligation step.

After ligation, the vector with the foreign gene now inserted is purified and transformed into a suitable host cell. A preferred transformation method is electroporation. Electroporation may be carried out using methods known in the art and described, for example, in U.S. Pat. No. 4,910,140; U.S. Pat. No. 5,186,800; U.S. Pat. No. 4,849,355; U.S. Pat. No. 5,173,158; U.S. Pat. No. 5,098,843; U.S. Pat. No. 5,422,272; U.S. Pat. No. 5,232,856; U.S. Pat. No. 5,283,194; U.S. Pat. No. 5,128,257; U.S. Pat. No. 5,750,373; U.S. Pat. No. 4,956,288 or any other known batch or continuous electroporation process. More than one (a plurality) electroporation may be conducted to increase the amount of DNA which is transformed into the host cells. Repeated electroporations are conducted as described in the art. See Vaughan et al. (1996) *Nature Biotechnology* 14:309-314. The number of additional electroporations may vary as desired from several (2,3,4, . . . 10) up to tens (10, 20, 30, . . . 100) and even hundreds (100, 200, 300, . . . 1000). Repeated electroporations may be desired to increase the size of a combinatorial library, e.g. an antibody library, transformed into the host cells.

Preferably, for library construction, the DNA is present at a concentration of 25 micrograms/mL or greater. More preferably, the DNA is present at a concentration of about 30 micrograms/mL or greater, more preferably at a concentration of about 70 micrograms/mL or greater and even more preferably at a concentration of about 100 micrograms/mL or greater even up to several hundreds of micrograms/mL. Generally, the electroporation will utilize DNA concentrations in the range of about 50 to about 500 micrograms/mL. A time constant during electroporation greater than 3.0 milliseconds (ms) results in a high transformation efficiency.

The DNA is preferably purified to remove contaminants. The DNA may be purified by any known method, however, a preferred purification method is the use of DNA affinity purification. The purification of DNA, e.g., recombinant plasmid DNA, using DNA binding resins and affinity reagents is well known and any of the known methods can be used in this invention (Vogelstein, B. and Gillespie, D. (1979) *Proc. Natl. Acad. Sci. USA* 76:615; Callen, W. (1993) *Strategies* 6:52-53). Commercially available DNA isolation and purification kits are also available from several sources including Stratagene (CLEARCUT Miniprep Kit), and Life Technologies (GLASSMAX DNA Isolation Systems). Suitable nonlimiting methods of DNA purification include column chromatography (U.S. Pat. No. 5,707,812), the use of hydroxylated silical polymers (U.S. Pat. No. 5,693,785), rehydrated silica gel (U.S. Pat. No. 4,923,978), boronated silicates (U.S. Pat. No. 5,674,997), modified glass fiber membranes (U.S. Pat. No. 5,650,506; U.S. Pat. No. 5,438,127), fluorinated adsorbents (U.S. Pat. No. 5,625,054; U.S. Pat. No. 5,438,129), diatomaceous earth (U.S. Pat. No. 5,075,430), dialysis (U.S. Pat. No. 4,921,952), gel polymers (U.S. Pat. No. 5,106,966) and the use of chaotropic compounds with DNA binding reagents (U.S. Pat. No. 5,234,809). After purification, the DNA is eluted or otherwise resuspended in water, preferably distilled or deionized water, for use in electroporation at the concentrations of the invention. The use of low salt buffer solutions is also contemplated.

Any suitable cells which can be transformed by electroporation may be used as host cells in the method of the present invention. Suitable host cells which can be transformed include gram negative bacterial cells such as *E. coli*. Suitable *E. coli* strains include JM101, *E. coli* K12 strain 294 (ATCC number 31,446), *E. coli* strain W3110 (ATCC number 27,325), *E. coli* X1776 (ATCC number 31,537), *E. coli* XL-1Blue (Stratagene), and *E. coli* B; however many other strains of *E. coli*, such as XL1-Blue MRF', SURE, ABLE C, ABLE K, WM1100, MC1061, HB101, CJ136, MV1190, JS4, JS5, NM522, NM538, and NM539, may be used as well. Cells are made competent using known procedures. Sambrook et al., above, 1.76-1.81, 16.30.

Cell concentrations of about $10^{10}$ colony forming units (cfu)/mL of viable living cells and greater are preferably used for electroporation. More preferably, the viable cells are concentrated to about $1 \times 10^{11}$ to about $4 \times 10^{11}$ cfu/mL. Preferred cells which may be concentrated to this range are the SS320 cells described below. Cells are preferably grown in culture in standard culture broth, optionally for about 6-48 hrs (or to $OD_{600}=0.6-0.8$) at about 37° C., and then the broth is centrifuged and the supernatant removed (e.g. decanted). Initial purification is preferably by resuspending the cell pellet in a buffer solution (e.g. HEPES pH 7.4) followed by recentrifugation and removal of supernatant. The resulting cell pellet is resuspended in dilute glycerol (e.g. 5-20% v/v) and again centrifuged to form a cell pellet and the supernatant removed. The final cell concentration is obtained by resuspending the cell pellet in water or dilute glycerol to the desired concentration.

A particularly preferred recipient cell for the electroporation is a competent *E. coli* strain containing a phage F' episome. Any F' episome which enables phage replication in the strain may be used in the invention. Suitable episomes are available from strains deposited with ATCC or are commercially available (CJ236, CSH18, DH5alphaF', JM101, JM103, JM105, JM107, JM109, JM110), KS1000, XL1-BLUE, 71-18 and others ). Strain SS320 was prepared by mating MC1061 cells with XL1-BLUE cells under conditions sufficient to transfer the fertility episome (F' plasmid) of XL1-BLUE into the MC1061 cells. In general, mixing cultures of the two cell types and growing the mixture in culture medium for about one hour at 37° C. is sufficient to allow mating and episome transfer to occur. The new resulting *E. coli* strain has the genotype of MC1061 which carries a streptomycin resistance chromosomal marker and the genotype of the F' plasmid which confers tetracycline resistance. The progeny of this mating is resistant to both antibiotics and can be selectively grown in the presence of streptomycin and tetracycline. Strain SS320 has been deposited with the American Type Culture Collection (ATCC), 10801 University Boulevard, Manassas, Va., USA on Jun. 18, 1998 and assigned Deposit Accession No. 98795.

This deposit of strain SS320 was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited cultures is not to be construed as a license to practice the invention in contravention of the rights granted under the authority of any government in accordance wish its patent laws.

Oligonucleotide-mediated mutagenesis is a preferred method for preparing the substitution, deletion, and insertion variants of the invention. This technique is well known in the art as described by Zoller et al. (1987) *Nucleic Acids Res.* 10: 6487-6504. Briefly, a gene encoding a protein fusion or heterologous polypeptide is altered by hybridizing an oligonucleotide encoding the desired mutation to a DNA template, where the template is the single-stranded form of the plasmid containing the unaltered or native DNA sequence of the gene. After hybridization, a DNA polymerase is used to synthesize an entire second complementary strand of the template which will thus incorporate the oligonucleotide primer, and will code for the selected alteration in the gene. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (1978) *Proc. Nat'l. Acad. Sci. USA* 75: 5765.

The DNA template is generated by those vectors that are derived from the bacteriophage used in the phage display system, e.g. bacteriophage M13 vectors (the commercially available M13 mp18 and M13 mp19 vectors are suitable), or those vectors that contain a single-stranded phage origin of replication; examples are described by Viera et al. (1987) *Meth. Enzymol.* 153:3. Thus, the DNA that is to be mutated can be inserted into one of these vectors in order to generate single-stranded template. Production of the single-stranded template is described in sections 4.21-4.41 of Sambrook et al.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of the gene, and the other strand (the original template) encodes the native, unaltered sequence of the gene. This heteroduplex molecule is then transformed into a suitable host cell, usually a prokaryote such as *E. Coli* JM101. After growing the cells, they are plated onto agarose plates and screened using the oligonucleotide primer radiolabelled with 32-Phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of, three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Cassette mutagenesis is also a preferred method for preparing the substitution, deletion, and insertion variants of the invention. The method is based on that described by Wells et al. (1985) *Gene* 34:315. The starting material is a plasmid (or other vector) containing the gene to be mutated. The codon (s) in the gene to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the gene. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of the gene. Vectors containing the mutated variants can be transformed into suitable host cells as described above.

The transformed cells are generally selected by growth on an antibiotic, commonly tetracycline (tet) or ampicillin (amp), to which they are rendered resistant due to the presence of tet and/or amp resistance genes in the vector.

Suitable phage and phagemid vectors for use in this invention include all known vectors for phage display. Additional examples include pComb8 (Gram et al. (1992) *Proc. Natl. Acad. Sci. USA* 89:3576-3580); pC89 (Felici et al. (1991) *J. Mol. Biol.* 222:310-310); pIF4 (Bianchi et al. (1995) *J. Mol. Biol.* 247:154-160); PM48, PM52, and PM54 (Iannolo. (1995) *J. Mol. Biol.* 248:835-844); fdH (Greenwood et al. (1991) *J. Mol. Biol.* 220:821-827); pfd8SHU, pfd8SU, pfd8SY, and fdISPLAY8 (Malik & Perham (1996) *Gene* 171:49-51); "88" (Smith (1993) *Gene* 128:1-2); f88.4 (Zhong et al. (1994) *J. Biol. Chem*, 269:24183-24188); p8V5 (Affymax); MB1, MB20, MB26, MB27, MB28, MB42, MB48, MB49, MB56: (Markland et al. (1991) *Gene* 109:13-19). Similarly, any known helper phage may be used when a phagemid vector is employed in the phage display system. Examples of suitable helper phage include M13-KO7 (Pharmacia), M13-VCS (Stratagene), and R408 (Stratagene).

After selection of the transformed cells, these cells are grown in culture and the vector DNA may then be isolated. Phage or phagemid vector DNA can be isolated using methods known in the art, for example, as described in Sambrook et al., *Molecular Cloning: A Laboratory Manual*, 2nd edition, (1989) Cold Spring Harbor Laboratory Press, Cold Spring Harbor, N.Y.

The isolated DNA can be purified by methods known in the art such as that described in section 1.40 of Sambrook et al., above and as described above. This purified DNA can then be analyzed by DNA sequencing. DNA sequencing may be performed by the method of Messing et al. (1981) *Nucleic Acids Res.* 9:309, the method of Maxam et al. (1980) *Meth. Enzymol.* 65:499, or by any other known method.

V. Applications

The various aspects and embodiments of the present invention demonstrate the advantages of a novel model system for rationally designing and analyzing peptides of defined structural features. The combinatorial libraries comprising such peptides and methods of using thereof provide useful information and tools for exploring the basic structure-activity relationships involved in almost all biological molecular interactions. The peptides disclosed herein or generated according to the disclosure of the invention can be candidates for various biological or therapeutic agents, including but not limited to, enzyme inhibitors, ligand antagonists, ligand agonists, toxins, and immunogens.

The following examples are provided by way of illustration and not by way of limitation. All disclosures of the references cited herein are expressly incorporated herein by reference in their entirety.

EXAMPLES

Example 1

Design of a Structured, Disulfide-Constrained β-Hairpin Peptide Scaffold

In this example, we chose to investigate disulfide-constrained β-hairpins of the decamers in the form of $CX_8C$ as scaffolds for β-turn display. For our purpose, it is essential to design a structure compatible with many turn sequences. That is, residues other than those in the turn must significantly bias the peptide toward hairpin structure. Disulfide cyclization is helpful, although not sufficient to structure many peptides. Our initial objective was to determine whether the disulfide bond could be used not only as a covalent constraint, but also to nucleate a more extended interaction of the β-strands.

Materials and Methods

Peptide Synthesis. Peptides were synthesized using standard Fmoc chemistry on a Pioneer synthesizer (PE Biosystems), cleaved from resin with 5% triisopropylsilane in trifluoroacetic acid (TFA), and purified by reversed-phase HPLC (acetonitrile/$H_2O$/0.1% TFA). Peptide identity was confirmed by mass spectrometry. Peptides were converted to cyclic disulfides by dropwise addition of a saturated solution of $I_2$ in acetic acid and repurified by HPLC. Purified peptides eluted as single symmetric peaks on C18 analytical columns (0-40% acetonitrile in 40 minutes).

Cysteine Effective Concentration Measurements. Glutathione stock solutions were prepared by mixing 3 volumes of 0.2 M reduced glutathione (GSH) with 1 volume of 0.1 M oxidized glutatione (GSSG). Aliquots were stored at −80° C. and were stable for several months; use of a single batch eliminated any error in $\Delta\Delta G$ values that might arise from variability of total glutathione concentration. Thiol-disulfide equilibria were established by mixing 50 µL peptide stock (approximately 3 mM in water) with 50 µL glutathione stock, deoxygenating the acidic solution with vacuum/argon cycles from a Firestone valve, then adding 300 µL of deoxygenated buffer by syringe (0.2 M tris, pH 8.0; 1 mM EDTA; 67 mM tris base to titrate glutathione), followed by further deoxygenation of the mixture. The final pH of all reaction mixtures was 8.10±0.05. Solutions were stirred under argon and maintained at 20° C. in a water bath. After 1.5 h, successive aliquots (100 µL) were removed with a gastight syringe, immediately quenched by discharge into 400 µL of 3.1 mM HCl, and analyzed by HPLC with a minimum of delay. $C_{eff}$ values were calculated from the molar ratios of the reduced and oxidized forms of peptide and glutathione (peak area ratios corrected for absorbance differences measured by HPLC), assuming 0.025 M total glutathione monomer (i.e., neglecting the minor amount (<1%) of glutathione present in mixed disulfides with peptide):

$C_{eff}$=([peptide$_{ox}$]/[peptide$_{red}$])×([GSH]$^2$/[GSSG])

[GSH]+2[GSSG]=0.025 M

[GSSG]=0.025 M/{2+3.26 (GSH peak area/GSSG peak area)}

[peptide$_{ox}$]/[peptide$_{red}$]=equilibrium peak area ratio/absorbance ratio

Two or three samples from each reaction mixture were analyzed; there were no shifts in populations with time, and calculated $C_{eff}$ values typically varied by less than 5% (equivalent to 30 cal/mol uncertainty in $\Delta\Delta G$).

NMR Spectroscopy. NMR samples contained 5-10 mM peptide in 92% $H_2O$/8% $D_2O$ pH 5.1 and 0.1 mM 1,4-dioxane as chemical shift reference. All spectra were acquired on a Bruker DRX-500 or a Varian Unity-400 spectrometer at 15° C. 2QF-COSY, TOCSY and ROESY spectra were acquired as described (Cavanagh et al. (1995) *Protein NMR Spectroscopy, Principles and Practices* (Academic Press, San Diego) with gradient coherence selection (van Zijl et al. (1995) *J. Magn. Reson.* 113A:265-270), or excitation sculpting (Hwang & Shaka, (1995) *J. Magn. Reson.* 112A, 275-279.) for water suppression. Proton resonances were assigned by standard methods (Wüthrich (1986) *NMR of Proteins and Nucleic Acids* (John Wiley and Sons, New York). $3J_{H^N-H^\alpha}$ were obtained by fitting Lorentzian lines to the antiphase doublets of HN—$H^\alpha$ peaks in 2QF-COSY spectra processed to high digital resolution in $F_2$. $3J_{H^N-H^\alpha}$ were extracted from COSY-35 spectra acquired on $D_2O$ solutions of the peptides. Distance and dihedral angle restraints were generated as described (Skelton et al. (1994) *Biochemistry* 33:13581-13592). 100 initial structures were calculated using the hybrid distance geometry/simulated annealing program DGII (Havel et al. (1991) *Prog. Biophys. Mol. Biol.* 56:43-78.); 80 of these were further refined by restrained molecular dynamics using the AMBER all-atom forcefield implemented in DISCOVER as described previously (Skelton et al. (1994) *Biochemistry* 33:13581-13592.). 20 conformations of lowest restraint violation energy were chosen to represent the solution conformation of each peptide.

Structure Calculation. Structures were calculated with 78 ROE-derived distance restraints (10 medium- and 28 long-range restraints; upper bounds of 5.4, 4.3, 3.4 or 3.0 Å) and 12 dihedral angle restraints. The final 20 structures had average maximum violation of distance and dihedral angle restraints of 0.05±0.02 Å and 0.7±0.2°, respectively; RMS deviation from the experimental distance and dihedral angle restraints were 0.007±0.002 Å and 0.29±0.08°, respectively. The mean RMSD from the mean structure is 0.28±0.04 Å for N, $C^\alpha$, and C atoms of residues Cys1-Cys10 whilst 75% of residues had $\Phi\Psi$ values in the most favored portions of the Ramachandran plot (none were in the disallowed or generously allowed region) (Laskowski et al. (1993) *J. Appl. Crystallogr.* 26:283-291.).

NMR Analysis. NMR samples of CD4 peptides contained ~2 mM peptide in 92% $H_2O$/8% $D_2O$, pH 3.5 with 50 μM 3-(trimethylsilyl)-1-propane-1,1,2,2,3,3,-$d_6$-sulfonic acid (DSS) as a chemical shift reference. Spectra were acquired and analyzed as described above. The structure of cd2 was calculated from 84 (including 13 medium- and 23 long-range) ROE-derived distance restraints and 13 dihedral angle restraints. The average maximum violations of distance and dihedral angle restraints are 0.05±0.01 Å and 0.6±0.4°, respectively; the RMSDs from the experimental distance and dihedral angle restraints are 0.009±0.002 Å and 0.2±0.1°, respectively. The covalent geometry is good, with 74% of the $\Phi\Psi$ angles within the most favored and none in the disallowed or generously allowed regions of the Ramachandran plot (Laskowski et al. (1993) *J. Appl. Crystallogr.* 26:283-291).

Analysis of Sidechain Rotamers. Observation of both $^3J_{H^\alpha-H_\beta}1$ and $^3J_{H^\alpha-H_\beta}2$ in the range of 6-9 Hz indicates that a side chain does not occupy a single classical rotamer ($\chi 1 = -60°, +60°$ or $180°$), and most likely samples all three staggered rotamer wells. This is the situation for Trp3 and Leu8 of bhpw and Gln4, Phe7 and Leu8 of cd2. ROE peaks observed to these side chains represent a time-average over the range of $\chi 1$ values sampled. Not all of these conformations will give rise to readily observable ROE peaks, hence the structure calculation process will be biased towards those rotamers for which restraints could be obtained. For example, ROEs from Phe7 of cd2 are observed to protons in the opposite strand, thereby forcing Phe7 to lie in the $+60°$ rotamer well. Given the large number of backbone-backbone distance and $\Phi$ dihedral angle restraints, the structures calculated for bhpw and cd2 do accurately represent the solution conformation of these peptides, except in the over determination of some side chain orientations.

Results

In our survey of β-sheets from a set of 928 non-redundant protein structures, the mean $C^\beta$-$C^\beta$ distances between hydrogen-bonded and non-hydrogen bonded pairs of residues in adjacent strands were 4.82±0.58 and 5.37±0.56 Å, respectively, while the average $C^\beta$-$C^\beta$ distance in disulfide-bonded cysteines was 3.84 Å. Therefore, the $C^\beta$ atoms of opposing residues on antiparallel strands are normally too far apart for disulfide bond formation. Nonetheless, disulfide crosslinks are sometimes found between cysteines in the non-hydrogen-bonding register in β-sheets. We found 23 disulfide-bonded cysteine pairs joining adjacent antiparallel strands. In 14 of 23 cases, the disulfide packs tightly against the hydrophobic sidechain two residues before one (or both) of the cysteines (FIG. 1a). In 5 additional cases this hydrophobic site was occupied by a polar or charged residue with β and γ-methylenes (E, Q, or R). In particular, the sidechains of either leucine or an aromatic amino acid provided good shape complementarity to this characteristic disulfide conformation. Accordingly, we chose leucine as residue 8 in our model peptide (FIG. 1b), included threonines at positions 2 and 9 to promote an extended backbone conformation, and chose the turn sequence EGNK as a representative, but not overly strong, type II'β-turn. To determine the best cross-strand pairing with leucine, position 3 was varied.

Figure 2:
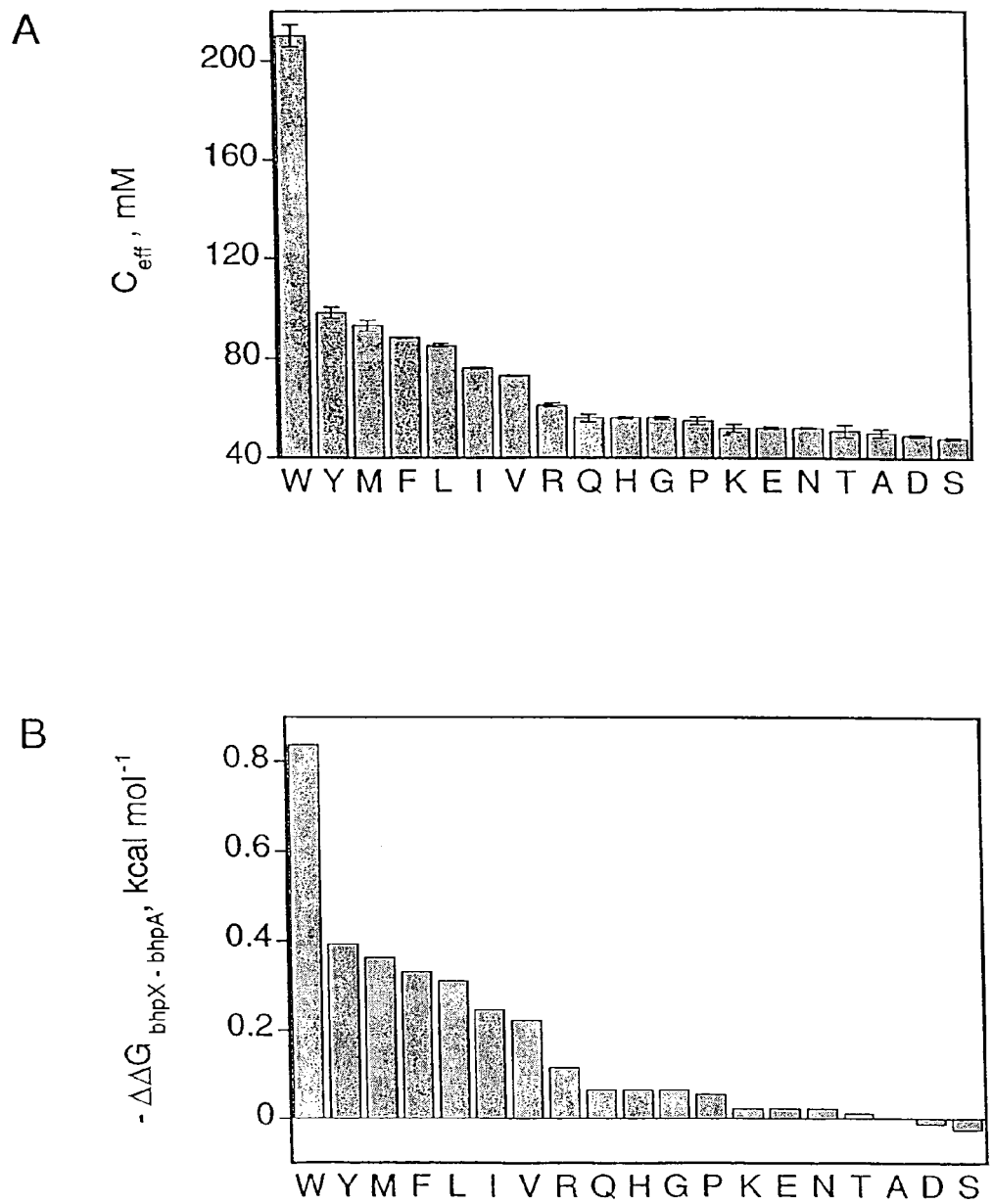
FIG. 2 shows the relative hairpin stability for substitution X in the bhp peptide sequence. (A) Cysteine effective concentrations ($C_{eff}$) relative to glutathione. Error bars are for ± one standard deviation; (B) Equilibrium free energy differences relative to the alanine peptide.

The presence of a disulfide provides a convenient probe for hairpin stability. Thiol-disulfide equilibria were measured relative to the reference thiol glutathione, yielding effective concentrations ($C_{eff}$) for the cysteine pairs. Larger values of $C_{eff}$ indicate an increased proximity, on average, of the cysteine thiols, consistent with formation of the hairpin structure. Peptide $C_{eff}$ values varied significantly for different residues at position 3 (FIG. 2a). Strikingly, tryptophan at position 3 strongly shifted the peptide equilibrium toward the oxidized form: this behavior was not caused by peptide aggregation. Scaling of the $C_{eff}$ values to that of the alanine analog ($-RT \ln\{C_{eff, X}/C_{eff, ala}\}$) yields free energy differences spanning >0.8 kcal/mol (FIG. 2b) that can be interpreted as the relative tendencies of the peptides to fold. These data do not, however, distinguish between effects on the folded and unfolded states of the peptide. For example, a given substitution might promote favorable side chain packing in the oxidized peptide, or simply bias toward an extended backbone conformation in the reduced peptide.

To assess whether the peptides were indeed forming β-hairpins, several of them were evaluated by $^1H$ NMR spectroscopy (Table 1). The tryptophan peptide (bhpw) exhibited all the hallmarks of a highly populated β-hairpin in terms of intense sequential $H^\alpha$-$H^N$ NOEs, numerous backbone cross-strand NOEs and large backbone scalar coupling constants ($^3J_{H^N_{-H^\alpha}}$>8.0 Hz) for strand residues. The $H^\alpha$ chemical shifts for Cys1 and Cys10 were downfield relative to values observed in unstructured peptides, indicating that the antiparallel strands encompass these terminal residues. The other peptides studied were judged to have a lower population of hairpin structure (see Table 1). Interestingly, the NMR data correlate well with $C_{eff}$ (Table 1); thus, the disulfide exchange assay provides a useful quantitation of the degree of hairpin structure in the oxidized peptides.

TABLE 1

Comparison of cysteine effective concentrations ($C_{eff}$) and $^1H$ NMR data for selected model hairpin peptides

| Residue 3 (X, FIG. 1b) | $C_{eff}$, mM | No. of $^3J H^N$ - $H^\alpha$ > 8 Hz | δ (Cys1 $H^\alpha$), ppm | δ (Cys10 $H^\alpha$), ppm |
|---|---|---|---|---|
| Trp bhpW | 210 ± 4 | 7 | 5.20 | 5.00 |
| Tyr | 98 ± 2 | 7 | 5.07 | 4.91 |
| Phe | 88 ± 0 | 5 | 5.07 | 4.92 |
| Leu | 85 ± 1 | 6 | 5.04 | 4.89 |
| Val | 73 ± 0 | 4 | 4.97 | 4.85 |
| Lys | 52 ± 2 | 3 | 4.92 | 4.82 |
| Asn | 52 ± 1 | 3 | 4.84 | 4.76 |
| random coil | | 0 | 4.71 | 4.71 |

The maximum number of strand residues with $^3J_{H^N\text{-}H^\alpha}$>8 Hz is 8; for the tryptophan peptide (bhpW), the Leu8 coupling constant is 7.9 Hz. Random coil coupling constants are taken from Smith et al. (Smith et al. (1996) *J. Mol. Biol.* 225:494-506.). Random coil $H^\alpha$ chemical shifts are taken from Wishart et al. (Wishart et al. (1992) *Biochemistry* 31:1647-1651).

Example 2

Figure 3:
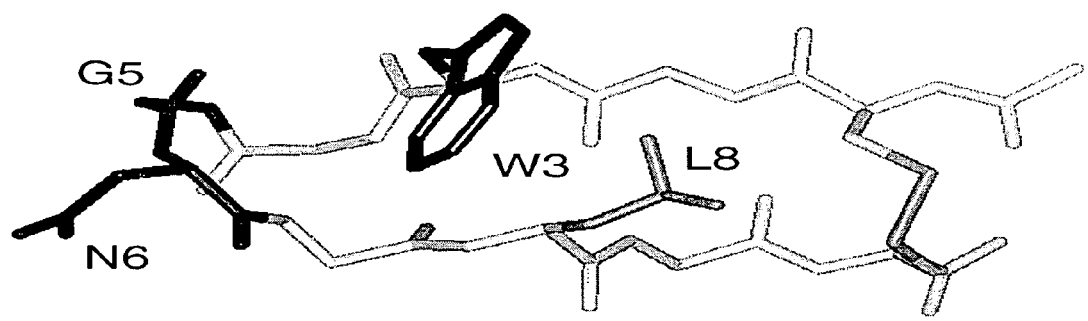
FIG. 3 depicts NMR structure (minimized mean) of disulfide-cyclized hairpin bhpW. Sidechain W3 and the central turn residues G5 and N6 are shown in black. Sidechain L8 and the disulfide are shown in gray. Sidechains for the hydrogen-bonded residues (T2, E4, K7, T9) have been omitted for clarity.

Transfer of Alternative Tetrapeptide Turn Sequences onto the Hairpin Scaffold Structures calculated for bhpw according to Example I revealed a well formed antiparallel hairpin with a type II' turn (Gly5-Asn6), and hydrophobic contacts between the side chains of Cys1, Trp3, Leu8 and Cys10 (FIG. 3). Thermodynamic analysis of bhpW stability was complicated by the failure of the oxidized peptide to unfold fully, either at high temperature or in the presence of chemical denaturants. Nevertheless, we estimate the hairpin conformation to be highly populated, most likely>80%, at 15° C. Because of its structural stability, we have chosen bhpw for investigation as a turn display scaffold. Accordingly we tested whether a different turn sequence could be structured by the bhpw strand sequences.

A recent crystal structure of HIV gp120 bound to a neutralizing antibody and to human CD4 revealed details of the contact surfaces (Kwong et al. (1998) *Nature* 393:648-659.). As had been anticipated from numerous mutagenesis studies, the CD4 region most important for gp120 binding is the C'-C" hairpin loop (residues 37-46), with the critical Phe43 side chain extending from the protein surface. In fact, CD4 residues 40-48 contribute 63% of the surface area buried in the interface, with 23% of the total contributed by Phe43 (Kwong et al. (1998) *Nature* 393:648-659.). Unexpectedly, there is a large cavity in gp120, behind the Phe43 binding site, that is lined with hydrophobic residues. It seemed possible that a structured peptide based on the C'-C" turn might bind to gp120 and if so, might be a starting point for designing ligands that extend into the cavity seen in the crystal structure.

Figure 4A:
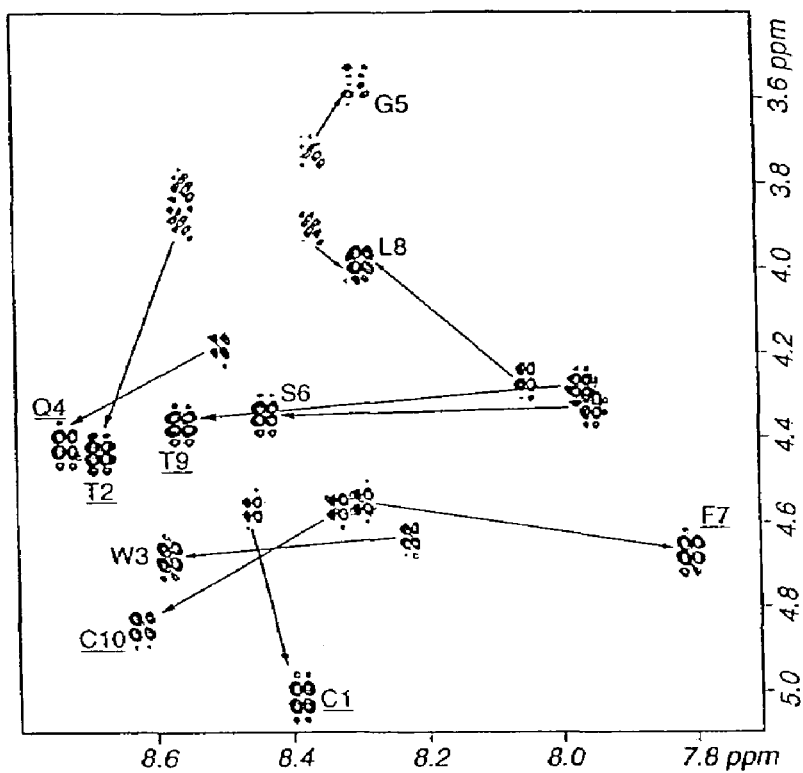
FIG. 4 (A-B) depicts NMR analysis of CD4 peptides. (A) Overlay of the fingerprint region of the COSY spectra for cd1 and cd2. (B) NMR structure ensemble for cd2 (20 models; two orthogonal views) shown superimposed on CD4 residues 37-46 from the crystal structure of gp120-bound CD4 (PDB entry 1GC1).
Figure 4B:
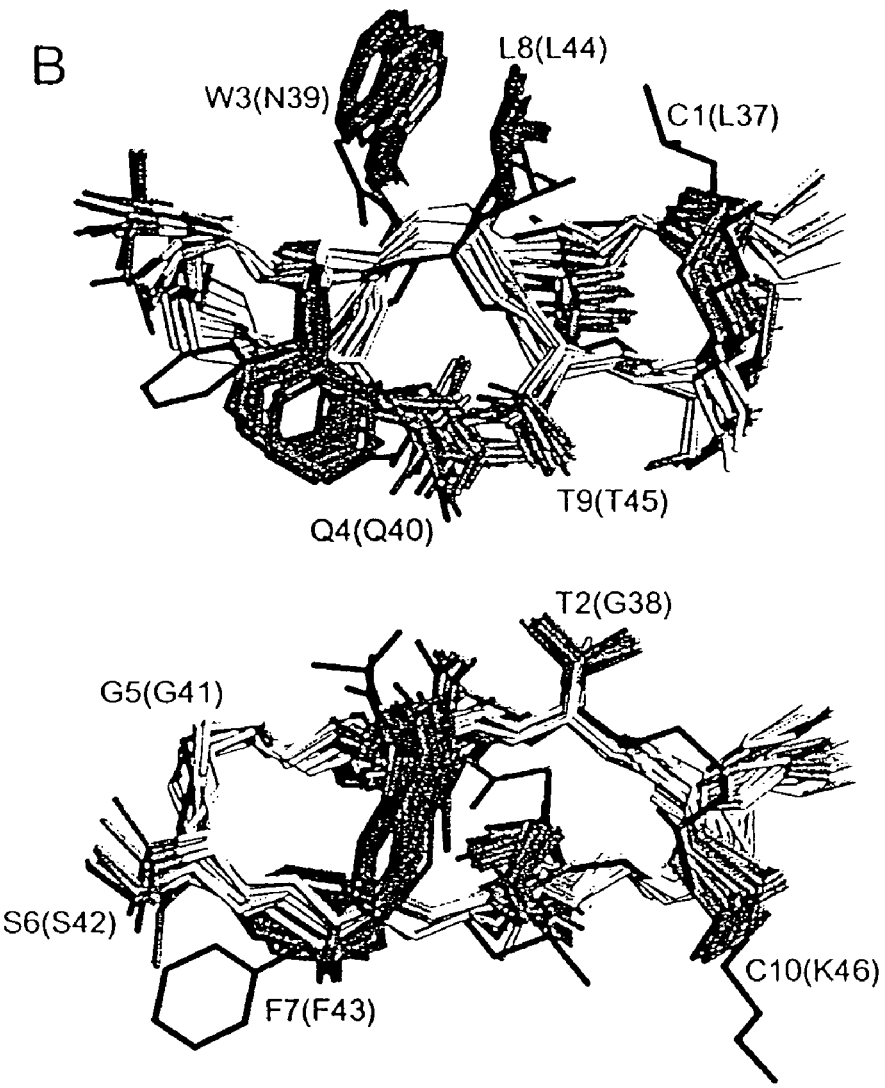

We synthesized a disulfide-constrained peptide based on the native sequence of the CD4 hairpin (residues 38-45, cd1 in Table 2) and found it to be essentially unstructured in solution (FIG. 4a). We then made the substitutions G2T and N3W, to match the corresponding residues in bhpw (cd2, Table 2); residues L8 and T9 are already present in the native CD4 sequence. Peptide cd2 is well-ordered, adopting a hairpin structure with a type II' turn (FIG. 4). In FIG. 4A, peak assignments for cd2 are shown; arrows indicate the location of the corresponding crosspeak in cd1. Those cd2 residues with $^3J_{H^N\text{-}H}>8.3$ Hz are underlined; all cd1 residues have backbone coupling constants between 5.9 and 7.7 Hz. From the measured $C_{eff}$ values, the CD4 turn (QGSF) destabilizes the model hairpin (EGNK turn) by 0.5 kcal/mol, and we found that both the T2 and W3 substitutions were necessary for stable hairpin structure (Table 2). Importantly, comparison of the peptide structure with that of CD4 indicates that the backbone conformations are essentially the same, within the uncertainties of the structure determinations (0.93 Å RMSD; FIG. 4B). FIG. 4B shows the NMR structure ensemble for cd2 (20 models; two orthogonal views) shown superimposed on CD4 residues 37-46 (red) from the crystal structure of gp120-bound CD4. The RMSD for the 20 models, with respect to the mean coordinates for the backbone atoms of residues 1-10, is 0.50±0.09 Å; comparison of the mean coordinates of residues 1-10 with residues 37-46 of CD4 from the crystal structure yields an RMSD of 0.93 Å. Note that the $^3J_{H^{58}\text{-}H}$ coupling constants for Phe7 of cd2 indicate that this sidechain is not fixed in the rotamer seen in the ensemble; the Phe7 sidechain adopts multiple conformations in solution, undoubtedly sampling that observed in the co-crystal structure. This demonstrates that the peptide scaffold correctly presents the CD4 β-turn.

TABLE 2

Comparison of bhpW and peptides based on the CD4 C'-C" loop

| Peptide | $C_{eff}$ (mM) | $[\theta]_{215}$ deg cm² dmol⁻¹ | No. of $^3J_{H^N}$ – $H^\alpha$ > 8 Hz | δ (Cys$_N$ H$^\alpha$) (ppm) | δ (Cys$_C$ H$^\alpha$) (ppm) |
|---|---|---|---|---|---|
| Ac-C<u>TW</u>EGNKLTC-NH₂ (SEQ ID NO:2) bhpW | 210 ± 4 | −19,800 | 7 | 5.20 | 5.00 |
| SC<u>TW</u>EGNKLTCK-NH₂ (SEQ ID NO:3) | 273 ± 2 | −17,400 | n.d. | n.d. | n.d. |
| Ac-C<u>GN</u>QGSFLTC-NH₂ (SEQ ID NO:4) cd1 | n.d. | n.d. | 0 | 4.66 | 4.66 |
| Ac-C<u>TW</u>QGSFLTC-NH₂ (SEQ ID NO:5) cd2 | n.d. | −15,800 | 6 | 5.08 | 4.93 |
| SC<u>GN</u>QGSFLTCK-NH₂ (SEQ ID NO:6) cd1a | 45 ± 4 | −1,500 | 0 | 4.80 | 4.72 |
| SC<u>TN</u>QGSFLTCK-NH₂ (SEQ ID NO:7) | n.d. | −5,000 | 2 | 4.96 | 4.79 |
| SC<u>GW</u>QGSFLTCK-NH₂ (SEQ ID NO:8) | 48 ± 0 | −6,100 | 3 | 5.00 | 4.88 |
| SC<u>TW</u>QGSFLTCK-NH₂ (SEQ ID NO:9) cd2a | 120 ± 0 | −14,000 | 6 | 5.36 | 5.14 |

Terminal serine and lysine residues were added to improve the solubility of some variants of the CD4 peptide, which are otherwise uncharged. A similar modification was made to bhpW as a control. Non-turn residues that differ between bhpW and the CD4 loop are underlined. Coelution of reduced and oxidized peptides prevented measurement of $C_{eff}$ for the T2, N3 variant of the CD4 peptide. Circular dichroism spectra were acquired at 10° C. with an Aviv Instruments, Inc. Model 202 spectrophotometer; peptide concentrations were 20 µM in 20 mM potassium phosphate, pH 7.0.

[n. d.: not determined; $Cys_N$ $H^\alpha$: $H^\alpha$ chemical shift for the more N-terminal cysteine (Cys1 or Cys2); $Cys_C$ $H^\alpha$: $H^\alpha$ chemical shift for the more C-terminal cysteine (Cys10 or Cys11)]

Two other turn sequences evaluated were VWQL from the F-G loop domain 2 of human Fc-epsilon-RI, and GPLT from the EPO agonist peptide EMP1. All three turns were evaluated in the trp peptide scaffold and in cyclized peptides whose sequence matched more closely the native parent hairpin loops:

| | | |
|---|---|---|
| SCGNQGSFLTCK-NH$_2$ (SEQ ID NO:10) | CD4 peptides | a |
| SCTWQGSFLTCK-NH$_2$ (SEQ ID NO:11) | | b |
| Ac-CTKVWQLWTC-NH$_2$ (SEQ ID NO:12) | Fc-epsilon-RI peptides | c |
| SCTWVWQLLTCK-NH$_2$ (SEQ ID NO:13) | | d |
| SCHFGPLTWVCK-NH$_2$ (SEQ ID NO:14) | EMP1 peptides | e |
| SCTWGPLTLTCK-NH$_2$ (SEQ ID NO:15) | | f |

Figure 5:
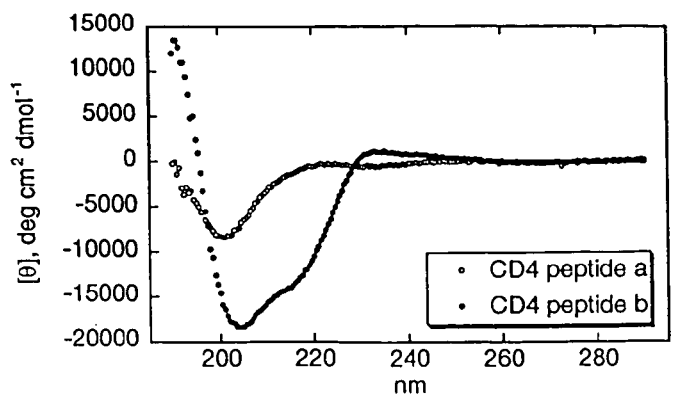
FIG. 5 shows circular dichroism spectra of three peptide pairs of Example 2.
Figure 5:
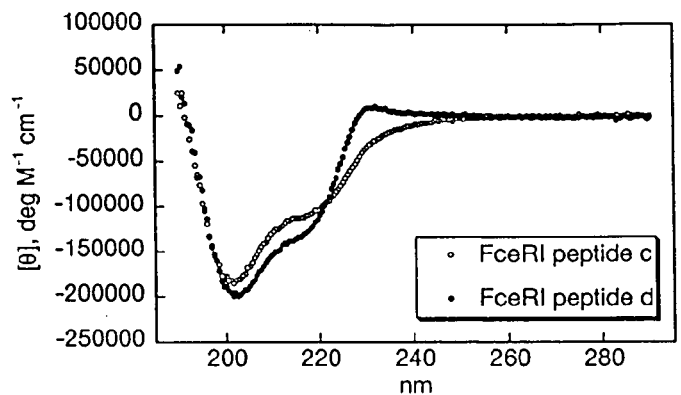
Figure 5:
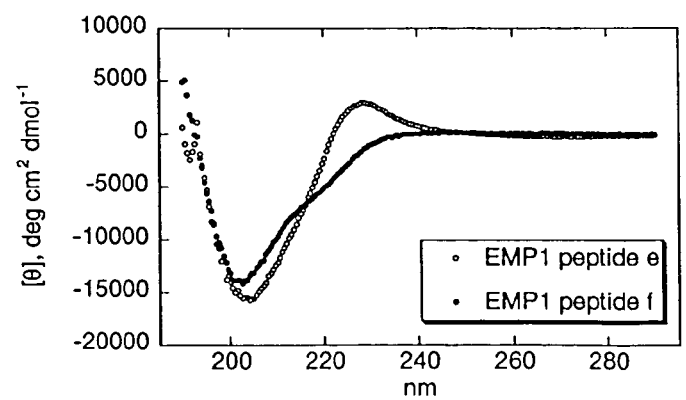

Circular dichroism spectra show that in each case, the designed trp hairpin scaffold yields a more structured peptide (FIGS. 5a-c). NMR data are consistent with increased hairpin structure in the peptides, demonstrating that the scaffold can bias a variety of "difficult" turns toward structured states.

Other common turns that can be presented on the hairpin scaffold include gamma-turns (3 amino acids), bulged turns (5 or 6 amino acids), and longer hairpins (8 amino acids). Other turn lengths are known and are also be compatible with the scaffold.

The results in Example 1 and 2 demonstrate that optimization of a single strand position in a small disulfide-constrained hairpin is sufficient to convert a very poorly structured molecule to one that is highly structured (−ΔΔG>0.8 kcal/mol). The stem portion of the structured hairpin, -CTW----LTC-, does not require an optimized turn sequence; thus, it is a suitable scaffold for display of β-turn libraries and for studying particular turns that might not otherwise be highly populated. Importantly, only natural amino acids are required, so turn libraries may be displayed on phage.

It is interesting to compare the substitution energies we report here with previous studies on β-sheet systems. Although the magnitude of the energy differences is similar, the rank order we obtain does not correlate with experimental α-propensity scales or with observed residue pair frequencies in known β-sheets (Hutchinson et al. (1998) *Protein Sci.* 7:2287-2300, Wouters, M. A. & Curmi, P. M. G. (1995) *Proteins* 22:119-131). In particular, tryptophan is unexceptional in such scales. These differences stress that average trends in typical protein domains may not apply directly to small peptides in which most residues are highly solvent exposed, complicating the use of such information in de novo design. Furthermore, ΔΔG rank order does not correlate well with increasing non-polar surface area of the side chains, although the preferred residues are hydrophobic.

Finally, the hairpin stem is very small, yet the combination of disulfide and cross-strand tertiary contact imparts a structural bias exceeding that of a disulfide alone, e.g. $CX_4C$. Although it is known that some particular sequences (e.g., VVVV) (Milburn et al. (1988) *Int. J. Peptide Protein Res.* 31:311-321.) cannot adopt turn conformations compatible with our hairpin, it is also true that very few of the turn sequences observed in proteins have been shown to adopt well defined turn conformations in isolated peptides. We have demonstrated a simple strategy to increase this number. We envision that hairpin libraries with randomized turn sequences (e.g., $XCTWX_4LTCX$) might yield structured ligands whose binding determinants could be transferred readily to small synthetic turn mimetics or even used directly to identify small-molecule leads for high-throughput affinity optimization (Rohrer et al. (1998) *Science* 282: 737-740).

Example 3

Figure 6:
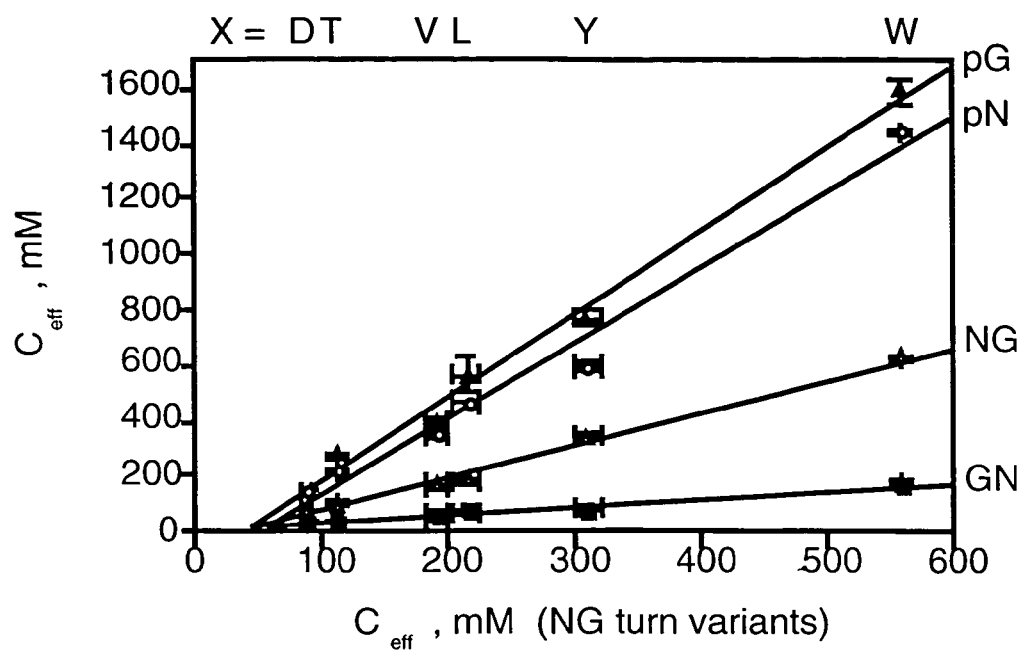
FIG. 6 shows effective concentration ($C_{eff}$) values for substitutions X in the peptides of Example 3. The strand substitutions X are shown at the top of the graph, and the central residues of the turns are indicated to the right.

Quantification of the Relative Contributions from Turns and Cross-Strand Interactions In Example 1 above, substitutions were introduced into position 3 (X) of the model peptide bhp (peptide 1). This guest site is quite close in space to the type II' turn (gly-asn, FIG. 1). To further investigate whether hairpins with different turn sequences and geometries would have different residue preferences at the NHB guest site, the central gly-asn sequence in model peptide 1 is replaced with the type I' turn asn-gly (peptide 2) and the type II' turns D-pro-asn and D-pro-gly (peptides 3 and 4). Substitutions at position 3 (X) were chosen to span the range of hairpin stabilities we observed in the gly-asn series. $C_{eff}$ was measured as previously described in Example 1. The values we obtain for the different turns are compared in FIG. 6.

| | | | |
|---|---|---|---|
| Ac-CT X E GN KLTC- NH$_2$ (SEQ ID NO:16) | 1 | II' | |
| Ac-CT X E NG KLTC- NH$_2$ (SEQ ID NO:17) | 2 | I' | X = W, Y, L, V, T, D |
| Ac-CT X E pN KLTC- NH$_2$ (SEQ ID NO:18) | 3 | II' | p ≡ D-pro |
| Ac-CT X E pG KLTC- NH$_2$ (SEQ ID NO:19) | 4 | II' | |

In all cases, tryptophan at position 3 yields the largest $C_{eff}$ value for a given turn, demonstrating that its stabilizing influence is general. The large changes in $C_{eff}$ for the different cross-strand interactions (horizontal axis) and turn sequences (vertical axis) show that both can contribute significantly to stability in these cyclic hairpin peptides. Finally, there are striking linear correlations between data sets, indicating that substitutions at strand position 3 and the turn replacements make independent contributions to stability of the cyclic hairpin. These data suggest that the hairpin fold may be quite modular, which would significantly simplify hairpin design.

Relative turn energies can be calculated by comparing $C_{eff}$ for the appropriate pairs of peptides. However, the correlation in FIG. 6 allow the calculation of relative turn energies from the slopes, which should be less sensitive to experimental error. These values are listed in Table 3. Compared to asn-gly (type I'), gly-asn (type II') is less stablizing, while the D-pro-containing turns (also type II') enhance hairpin stability. In the one case where a comparison may be made, asn-gly vs. D-pro-gly, the ΔΔG value obtained here agrees reasonably well with that obtained by NMR. This suggests that the reference states assigned by Syud et al. (1999) *J Am Chem Soc* 121:11577 and their assumption of two-state folding are appropriate for their model system; however, defining such reference states is not always feasible.

TABLE 3

Turn Energies Relative to Asn-Gly in peptides 1-4

| turn sequence | $C_{eff}$ correlation | | ΔΔG, kcal mol$^{-1a}$ |
|---|---|---|---|
| | slope | $R^2$ | |
| asn-gly repeat[b] | 1.19 | 0.99 | −0.10 |
| gly-asn | 0.29 | 0.97 | 0.72 |
| D-pro-asn | 2.72 | 0.98 | −0.58 |
| D-pro-gly[c] | 3.01 | 0.99 | −0.64 |

[a]ΔΔG = −RT ln(slope), T = 293K. Slopes are from the plot in FIG. 2.
[b]Two completely independent sets of measurements were made for the asn-gly peptides in order to assess the reliability of the assay over time. ΔΔG for the two data sets (~100 cal mol$^{-1}$) may be taken as an estimate of the error in the turn energies reported here.
[c]ΔΔG may be compared to the value of −0.52 ± 0.11 kcal mol$^{-1}$ (277 K) recently reported by Syud et al. (1999) supra.

Alternatively, substitution energies for the strand position may be obtained by plotting the same data, grouped instead by the residue X (not shown). The correlations are again excellent, and the slopes yield the free energy changes (Table 4). The range of energies is larger than that reported in Example 1 for peptide 1 (1.42 vs. 0.85 kcal mol$^{-1}$). Much of the difference is traced to those substitutions at the bottom of the stability scale (particularly asp). The less stable of the gly-asn turn peptides are not detectably structured, and $C_{eff}$ assays do not register any difference between them. Thus, the data obtained in peptides with the stronger turn sequences provide a more complete view of the strand substitution energies.

TABLE 4

Relative Energetic Contributions from Strand Residue X

| residue X | slope[a] | ΔΔG, kcal mol$^{-1b}$ | ΔΔG, GN turn[c] |
|---|---|---|---|
| trp | 2.92 | −0.62 | −0.53 |
| tyr | 1.27 | −0.14 | −0.08 |
| val | 0.66 | 0.24 | 0.09 |
| thr | 0.45 | 0.46 | 0.30 |
| asp | 0.25 | 0.80 | 0.32 |

[a]$C_{eff}$ values were plotted against those of leucine peptides 1-4.
[b]ΔΔG = −RT ln(slope), T = 293K.
[c]ΔΔG for the gly-asn turn series (ΔΔG = −RT ln {$C_{eff, x}$/$C_{eff, leu}$}), as described in Example 1.

Figure 7:
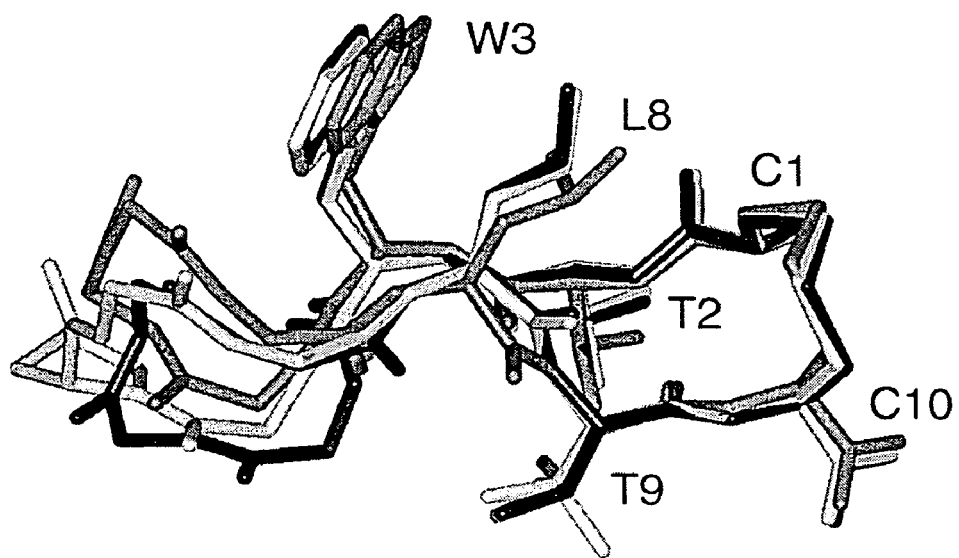
FIG. 7 depicts minimized mean structures of the tryptophan analogs of peptides in Example 3 overlaid on the backbone atoms of residues 1-3 and 8-10 (RMSD of 0.36 and 0.30 Å for 1 with respect to 2 and 3, respectively). Peptide 1 is in grey; peptide 2 is in black; and peptide 3 is in white. For clarity, non-proline side chain atoms are not shown for the four turn residues.

In order to assess how the turn types affect the hairpin structure, the tryptophan analogs of 2 and 3 were characterized by NMR spectroscopy, and structures were calculated as described in Example 1 for peptide 1. The comparison of minimized mean structures in FIG. 7 reveals that the backbone and side chain conformations are very similar for the non-turn residues (RMSD ~0.3 Å) regardless of the type of turn present. Thus, consistent with the linear correlations in $C_{eff}$ (FIG. 6), these three turns do not exert any structural influence on the adjacent strands.

The importance of the turn sequence and good cross-strand pairing to hairpin structure has been addressed in many model studies. However, there is little quantitative data or systematic evaluation of residue substitutions. Our data show that, for these simple cyclic peptides, substitutions in a strand site and in the turn conform to simple linear free-energy relationships and have independent and additive effects on hairpin stability. This is unexpected, given their proximity in the structure (FIGS. 3 and 7) and the reported sensitivity of calculated turn energies to features of the protein anchorage (Freidinger, R. M. (1999) *Curr. Opin. Chem. Biol.* 3:395-406). Nonetheless, it would appear that coupling between these turns and the strands is negliglible compared to the large influence each exerts alone. This suggests that β-hairpin stability may be understood by separate analysis of these components.

Example 4

Quantification of Energetic Contributions from Cross-Strand Residues

The results of above Examples revealed tryptophan to be quite stabilizing in the non hydrogen-bonded (NHB) strand site X of peptide 1, when paired with a cross-strand leucine. The tryptophan peptide (bhpW) was highly structured in water, adopting the intended hairpin conformation (FIG. 3). Here we investigate the relationship between the NHB cross-strand residues. Remarkably, we find that residue preferences for the two structurally inequivalent sites are the same, and that specific pair interactions produce only minor deviations from the single site contributions. Accordingly, a tryptophan-tryptophan cross-strand pair appears to be optimal for hairpin stability.

Our observation of a stabilizing contribution from tryptophan prompted us to question how general the effect might be. The tryptophan in peptide bhpw (FIG. 3) is spatially near both the cross-strand leucine and the side chains of residues in the type II' turn. Therefore, it seemed possible that the effect of tryptophan might depend on stabilizing contacts with these other residues. In order to address this question, we reversed the hydrophobic pairs (peptide 5), varying the amino acid at position 8 (nearest the disulfide, FIG. 3) with leucine fixed at position 3. Effective concentrations ($C_{eff}$) of the cysteine thiols were determined as in our previous studies.

| | | |
|---|---|---|
| Ac-C T X E G N K L T C-NH$_2$ (SEQ ID NO:20) | 1 | |
| Ac-C T L E G N K X T C-NH$_2$ (SEQ ID NO:21) | 5 | X = W, Y, F, L, M, I, V, A |
| Ac-C T X E G N K W T C-NH$_2$ (SEQ ID NO:22) | 6 | |
| Ac-C T W E G N K X T C-NH$_2$ (SEQ ID NO:23) | 7 | |

Figure 8:
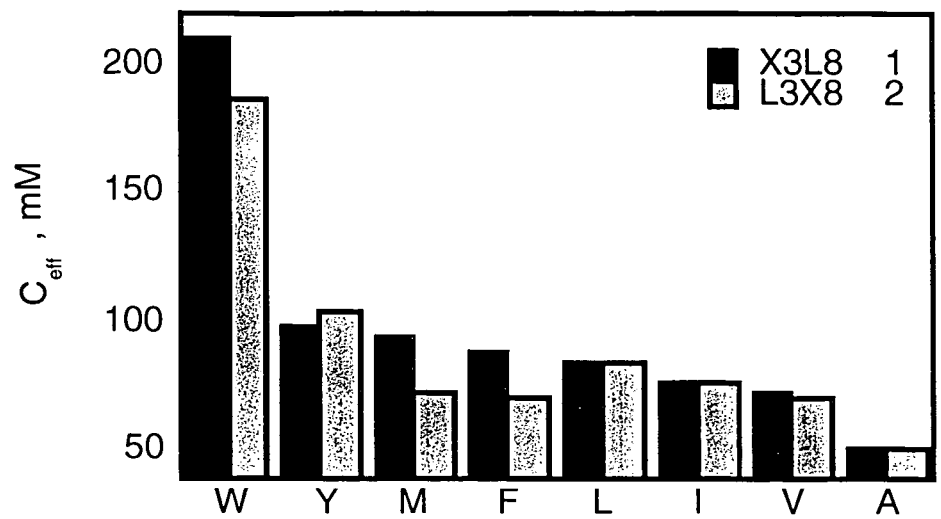
FIG. 8 (A-B) shows effective concentration ($C_{eff}$) values for peptides with hydrophobic pairs in non hydrogen-bonded (NHB) strand positions as described in Example 4. Values for substitutions paired with a cross-strand leucine are shown in (A); those for tryptophan pairs are shown in (B).
Figure 8:
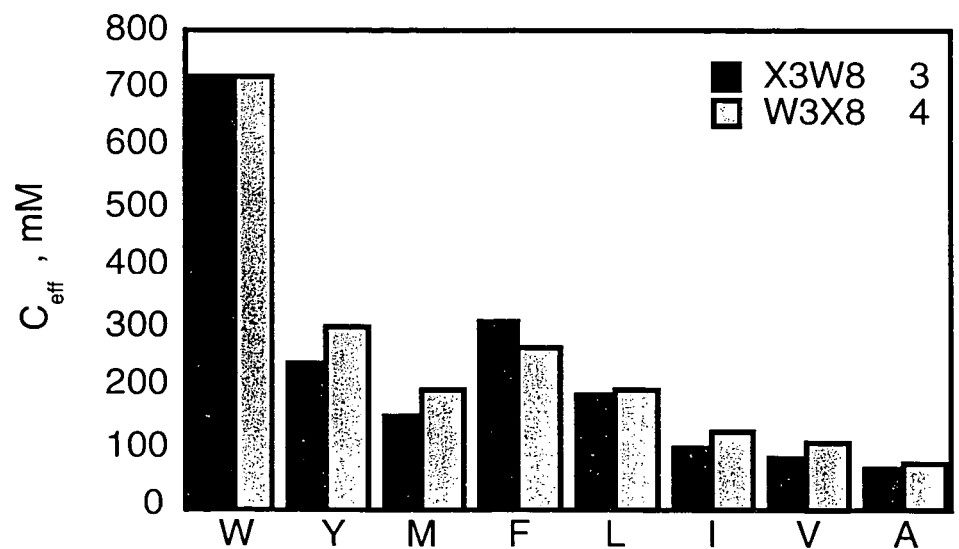

We find that tryptophan at position 8 is the most stabilizing of those residues tested (FIG. 8A). Significantly, the $C_{eff}$ values are quite close for the trp-leu and leu-trp pairs, indicating that the two arrangements are about equivalent energetically. This result appears to hold for other residue pairs with leucine: the rank order and numeric values of $C_{eff}$ are similar, but not exact, in the two series (FIG. 8A).

To test whether the equivalence of reversed hydrophobic pairs might be more general, we examined peptide series 6 and 7, in which residues are instead paired with a cross-strand tryptophan (FIG. 8B). As with leucine pairs, a close correspondence is seen between the two tryptophan series, both in rank order and value of $C_{eff}$. We conclude that the two cross-strand sites are essentially equivalent, despite the differences in side chain position relative to the turn and disulfide.

The two leucine series (1 and 5) may be compared to the tryptophan series (6 and 7). The trends in the two data sets are remarkably similar (FIGS. 8A and B), suggesting that the cross-strand residues contribute to stability in an independent manner. To explore this idea, we calculated free energy differences for substitutions in each of the peptide series relative to a reference peptide in that series ($\Delta\Delta G=-RT \ln (C_{eff} X/C_{eff, ref})$). Representative comparisons are plotted in FIG. 9.

Linear free energy relationships exist among the four data sets. This is seen in comparisons of particular cross-strand pairs switched between NHB sites 3 and 8, and also for comparisons of trp pairs with leu pairs in the same orientation (FIG. 3). (There is more scatter in the latter correlations.) The slopes ($\rho$) were determined using $\Delta\Delta G$ values scaled to two different reference peptides in each series (X=ala and trp). The $\rho\rho$values obtained were not greatly different (Table 5).

TABLE 5

Slopes ($\rho$) of Hammett plots for peptide series 1-4

| x-axis data set | $\rho$, X3 vs. X8 | $\rho$, leu vs. trp |
|---|---|---|
| W3X8[a] | 1.15 (1.11)[b] | 0.47 (0.43)[b] |
| L3X8 | 0.98 (0.86)[b] | — |
| X3W8 | — | 0.43 (0.32)[b] |

Figure 9:
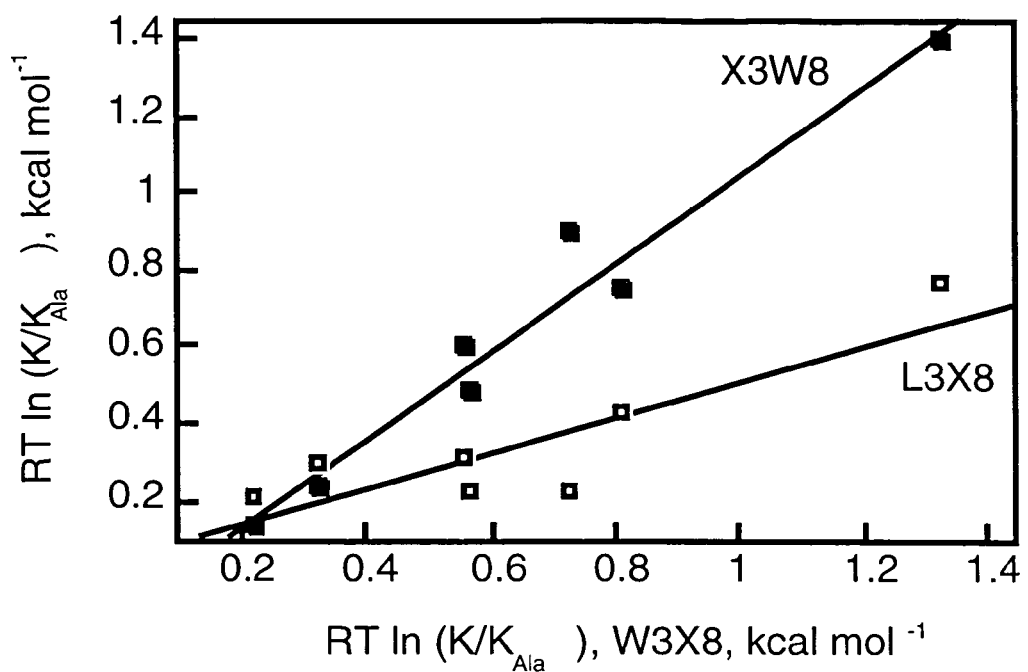
FIG. 9 depicts a Hammett plot comparing substitution free energy differences between the peptides of Example 4.

[a]Plots vs. W3X8 data are shown in FIG. 9. Values in parentheses were obtained using the tryptophan peptide in each series as internal reference (instead of the alanine peptide).

Consistent with the idea that positions 3 and 8 are equivalent, $\rho$ is near 1 for plots comparing these data. In contrast, when leu pairs are compared to trp pairs, $\rho$ is about 0.4. This means that for a given pair of residues X, the expected difference in hairpin stability is ~2.5-fold larger with trp as the cross-strand partner. Given these simple relationships, $\Delta\Delta G$ could be calculated for any substitution relative to a reference pair by multiplying a substituent energy $\sigma_X$ by $\rho$ for the cross-strand partner (see below). This is surprising, as these residues are within contact distance, and it has important implications for β-hairpin design.

Statistical analyses of HB and NHB cross-strand pairs in β-sheet proteins find many residue pairs to be positively or negatively correlated with high confidence. Largely in accord with the statistical preferences, protein mutagenesis studies have identified interaction energies as large as 1 kcal mol$^{-1}$ between HB pairs. It has been proposed that including cross-strand pairs preferred in proteins might improve stability or fix strand register in isolated β-hairpins.

Figure 10:
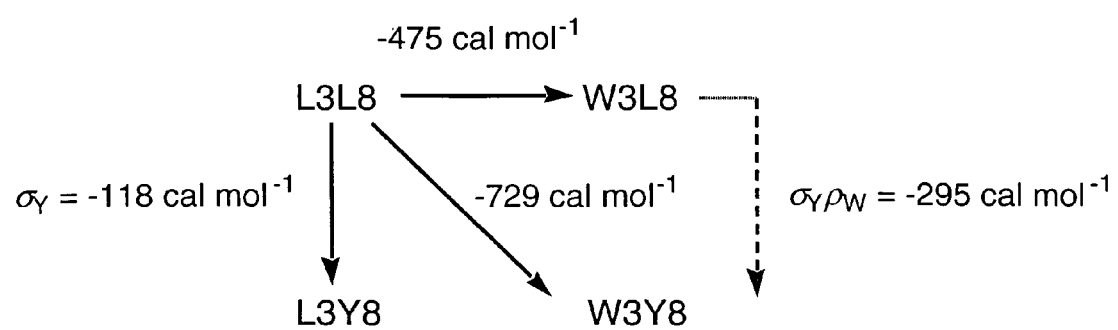
FIG. 10 shows double mutant analysis of the stability of W3Y8 relative to L3L8.

To look for these effects, we calculated pair interaction energies (FIG. 10). $C_{eff}$ ratios yield $\Delta\Delta G$ for the single or double substitutions. Typically, the difference between $\Delta\Delta G$ for the double substitution and $\Sigma\Delta\Delta G$ for the single substitutions is taken as an interaction energy. In the example shown, this would be −136 cal mol$^{-1}$ for the trp-tyr pair relative to a leu-leu reference state. If the single substitution energies are calculated sequentially, scaling by $\rho$ in the second step, the discrepancy is only +32 cal mol$^{-1}$ (insignificant in these experiments). For the phe-trp pair (compare FIG. 2, top and bottom), a similar analysis yields $\Delta\Delta\Delta G=-$ 253 cal mol$^{-1}$ when $\rho$ is included. This discrepancy is significant, and it suggests that there might be some specific structural advantage in pairing phe with trp (beyond the general superiority of trp). It is interesting that the discrepancy is small when compared to the total range of energies seen for single site substitutions (FIG. 9); we believe that such pair-specific effects (and experimental error) may explain the scatter in our correlations.

Our experiments show clearly that cross-strand tertiary contacts enhance hairpin stability. Notably, introduction of the trp-trp pair results in a large stabilization compared to our original peptide bhpw (FIGS. 3 and 8), and we believe that, despite its rarity in proteins, trp-trp is the optimal NHB pair for isolated hairpins. In most cases, the pair interaction energies we obtain through conventional double mutant analysis are adequately explained by differences in $\rho$. That is, these energies are not specific to a single pair, but instead reflect greater or lesser sensitivity to all residue substitutions opposite a given cross-strand partner. Therefore, we conclude that the combined single site preferences ($\sigma$ and $\rho$) are most important in predicting hairpin stability. Significantly, it should be possible to make these predictions from a limited basis set of experimental data.

Example 5

Construction of Phage-Displayed Libraries Based on the trp Peptide Scaffold

Libraries of random peptides fused to the gene 8 protein of the filamentous bacteriophage M13 were produced by Kunkel mutagenesis of plasmid pS1302b, a derivative of pS349 (U.S. patent application Ser. No. 09/380,448 which claims priority to U.S. Patent Application Nos. 60/103,514 filed Oct. 8, 1998 and 60/134,870 filed May 19, 1999, incorporated herein by reference). Plasmid pS1302b includes the tac promoter and malE leader sequence of pS349. The hGH sequence and Gly/Ser-rich linker sequence of pS349 were replaced by the sequence:

5'-TAA-TAA-TAA-ATG-GCT-GAT-CCG-AAC-CGT-TTC-CGC-GGT-AAA-GAT-CTG-GGT-GGC-GGT-ACT-CCA-AAC-GAC-CCG-CCA-ACC-ACT-CCA-CCA-ACT-GAT-AGC-CCA-GGC-GGT-3' (SEQ ID NO: 24)

The inserted sequence encodes three stop codons, the GD epitope tag, and a linker selected for high-level display of hGH. The plasmid also includes the lac repressor (lacI$^q$) and the ampicillin resistance gene from pS349. The oligonucleotide used to construct the library was:

5'-TCC-GCC-TCG-GCT-TAT-GCA-NNS-TGC-CT-TGG-NNS-NNS-NNS-NNS-CTG-ACT-TGT-NNS-ATG-GCT-GAT-CCG-AAC-CGT-3' (SEQ ID NO: 25)

The form of random peptides was therefore XCTWX$_4$LTCX. A library of 10$^9$ to 10$^{10}$ individual transformants was prepared by previously described methods (U.S. patent application Ser. No. 09/380,447). Approximately one-third of individual clones encoded a functional peptide sequence. The remainder were starting template, contained stop codons, or contained single nucleotide deletions. The library size is thus adequate to include several copies of each possible random sequence.

Example 6

Selection of Binding Peptides from the Structurally-Biased Library

Nunc MaxiSorp plates were coated overnight with 2 μg/mL rhuFc-epsilon-RI-IgG fusion in PBS. Plates were then blocked for one hour at room temperature with 0.5% BSA (Sigma A-7638) in PBS. Negative wells were prepared by coating only with 0.5% BSA. Phage ($10^{11}$ ifu per well) were added to ten each positive and negative wells and incubated with shaking for 20 h at room temperature. After extensive washing to remove nonspecifically-bound phage, binders were eluted by treatment with 0.2 M glycine, pH 2 for five minutes. The eluted phage were then neutralized by addition of TRIS base and used to infect a culture of E. coli (XL1-blue, Stratagene). Several cycles of binding, elution, and amplification (3-5 total) were conducted under similar conditions. 192 individual clones were screened for binding to the target receptor by incubation of phage supernatant with plates prepared as described for phage sorting. After washing, wells were treated with alpha-M13-HRP conjugate (Pharmacia Biotech 27-9421-01), and bound antibody was detected with OPD substrate (Sigma P-9187). Plate absorbance ($A_{492}$-$A_{405}$) was compared between positive and negative plates to identify those clones positive for receptor binding. Twelve such clones were identified.

The sequence of positive clones is identified by sequencing the encoding DNA. Peptides corresponding to the displayed sequences (i.e., 12-mers) are synthesized using standard solid-phase methods. The peptides are then assayed using an appropriate biological or binding assay to determine their potency. Peptides can be evaluated for hairpin structure using any of the known techniques outlined above: circular dichroism, NMR, or disulfide equilibrium. Substitutions may then be made in the peptides to determine the relative contributions of the selected turn residues to binding. Ideally, these substitutions will not disrupt the scaffold structure. Once the nature of the binding motif is understood, the turn sequence can then be transferred onto a suitable organic scaffold for further optimization.

While the invention has necessarily been described in conjunction with preferred embodiments, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein.

---

We claim:

1. An isolated structurally-constrained cyclic peptide, said cyclic peptide consisting of an amino acid sequence of C1-A1-A2-(A3)$_n$-A4-A5-C2 (SEQ ID NO: 1), wherein
   C1 and C2 are cysteines;
   A1, A2, A3, A4, and A5 are naturally occurring L-amino acids;
   A1 and A5 are independently amino acids W, Y, F, H, I, V, or T;
   A2 is amino acid W;
   A3 is any naturally occurring L-amino acid and n is an integer that is 4;
   A4 is amino acids W or L; and
C1 and C2 together form a disulfide bond thereby forming a cyclic peptide; the amino terminus of C1 is optionally protected with an amino protecting group; and the carboxy terminus of C2 is optionally protected with a carboxy protecting group; and wherein the cyclic peptide stabilizes a β-turn, β-hairpin, β-bulge, or γ-turn sequence.

2. The cyclic peptide of claim 1, wherein A1 or A5 is a β-branched residue having two non-hydrogen substituents on the β-carbon of the amino acid residue.

3. The cyclic peptide of claim 1, wherein A1 or A5 is T.

4. The cyclic peptide of claim 1, wherein A2 and A4 are W.

5. The cyclic peptide of claim 1, wherein (A3)$_4$ is EGNK, ENGK, QGSF or VWQL.

6. The cyclic peptide of claim 5, wherein A1 is T and A5 is T.

7. A fusion protein consisting of a structurally-constrained cyclic peptide, said cyclic peptide consists of the amino acid sequence X1-C1-A1-A2-(A3)$_n$-A4-A5-C2-X2, wherein
   C1 and C2 are cysteines;
   A1, A2, A3, A4, and A5 are naturally occurring L-amino acids;
   A1 and A5 are independently amino acids W, Y, F, H, I, V, or T;
   A2 and A4 are amino acid W;
   A3 is any naturally occurring L-amino acid and n is an integer that is;
   X1 and X2 each consists of any naturally occurring amino acid and each is independently a peptide of about 1 to 50 amino acids; and
C1 and C2 together form a disulfide bond and wherein the cyclic peptide stabilizes a β-turn, β-hairpin, β-bulge, or γ-turn sequence.

8. The cyclic peptide of claim 7, wherein A1 or A5 is T.

9. The cyclic peptide of claim 7, wherein A2 and A4 are W.

10. The cyclic peptide of claim 7, wherein (A3)$_4$ is EGNK, ENGK, QGSF or VWQL.

11. The cyclic peptide library of claim 10, wherein A1 is T and A5 is T.

* * * * *